(12) United States Patent
Razansky et al.

(10) Patent No.: US 9,572,497 B2
(45) Date of Patent: Feb. 21, 2017

(54) QUANTITATIVE MULTI-SPECTRAL OPTO-ACOUSTIC TOMOGRAPHY (MSOT) OF TISSUE BIOMARKERS

(75) Inventors: Daniel Razansky, Munich (DE); Vasilis Ntziachristos, Munich (DE)

(73) Assignee: Helmholtz Zentrum Munchen Deutsches Forschungszentrum fur Gesundheit und Umwelt (GMBH), Neuherberg (DE)

( * ) Notice: Subject to any disclaimer, the term of this patent is extended or adjusted under 35 U.S.C. 154(b) by 0 days.

(21) Appl. No.: 13/055,552

(22) PCT Filed: Jul. 25, 2008

(86) PCT No.: PCT/EP2008/006142
§ 371 (c)(1),
(2), (4) Date: Feb. 23, 2011

(87) PCT Pub. No.: WO2010/009747
PCT Pub. Date: Jan. 28, 2010

(65) Prior Publication Data
US 2011/0306857 A1 Dec. 15, 2011

(51) Int. Cl.
*A61B 8/00* (2006.01)
*A61B 5/00* (2006.01)

(52) U.S. Cl.
CPC .......... *A61B 5/0073* (2013.01); *A61B 5/0095* (2013.01)

(58) Field of Classification Search
CPC ....................................................... A61B 8/00
See application file for complete search history.

(56) References Cited

U.S. PATENT DOCUMENTS

| 4,255,971 A | 3/1981 | Rosenewaig |
| 4,343,993 A | 8/1982 | Bining et al. |

(Continued)

FOREIGN PATENT DOCUMENTS

| EP | 0459392 | 12/1991 |
| EP | 133703 | 8/2003 |

(Continued)

OTHER PUBLICATIONS

X Intes, V Ntziachristos, JP Culver, A Yodh, B Chance, "Projection access order in algebraic reconstruction technique for diffuse optical tomography", 2002, Phys. Med. Biol., vol. 47, pp. N1-N10.*

(Continued)

*Primary Examiner* — Rochelle Turchen
*Assistant Examiner* — Lisa Kinnard
(74) *Attorney, Agent, or Firm* — Stoel Rives LLP (57) ABSTRACT

A method of multi-spectral opto-acoustic tomography (MSOT) imaging of a target tissue including a target tissue biomarker includes illuminating the target tissue with an illumination device emitting at least one pulsed illumination pattern at several illumination wavelengths, detecting pressure signals from the target tissue biomarker with a detector device, wherein the pressure signals being produced in the target tissue are in response to the illumination, and reconstructing a quantitative tomographic image of a distribution of the target tissue biomarker in the target tissue, wherein the pressure signals are analyzed using a photon propagation model which depends on an illuminating light fluence in the target tissue and on the illumination wavelengths, at least one spectral processing scheme, and an inversion scheme providing the tomographic image.

27 Claims, 4 Drawing Sheets

(56) References Cited

U.S. PATENT DOCUMENTS

| | | | |
|---|---|---|---|
| 4,385,634 A | 5/1983 | Bowen | |
| 4,646,756 A | 3/1987 | Watmough et al. | |
| 4,770,183 A | 9/1988 | Groman et al. | |
| 4,986,275 A | 1/1991 | Ishida et al. | |
| 5,411,730 A | 5/1995 | Kirpotin et al. | |
| 5,840,023 A * | 11/1998 | Oraevsky et al. | 600/407 |
| 5,924,991 A | 7/1999 | Hossack et al. | |
| 6,070,093 A * | 5/2000 | Oosta et al. | 600/316 |
| 6,102,857 A | 8/2000 | Kruger | |
| 6,173,604 B1 | 1/2001 | Xiang | |
| 6,208,749 B1 | 3/2001 | Gutkowicz-Krusin et al. | |
| 6,216,025 B1 | 4/2001 | Kruger | |
| 6,263,221 B1 | 7/2001 | Chance et al. | |
| 6,424,410 B1 * | 7/2002 | Pelosi | 356/139.03 |
| 6,428,171 B1 * | 8/2002 | Aoki et al. | 356/634 |
| 6,445,453 B1 | 9/2002 | Hill | |
| 6,477,398 B1 | 11/2002 | Mills | |
| 6,498,492 B1 | 12/2002 | Rezvani | |
| 6,526,298 B1 * | 2/2003 | Khalil | A61B 5/0059 600/310 |
| 6,567,688 B1 | 5/2003 | Wang | |
| 6,615,063 B1 | 9/2003 | Ntziachristos et al. | |
| 6,641,798 B2 | 11/2003 | Achilefu et al. | |
| 6,662,040 B1 | 12/2003 | Henrichs et al. | |
| 6,700,459 B2 | 3/2004 | Raihn et al. | |
| 6,760,609 B2 | 7/2004 | Jacques | |
| 6,768,265 B1 | 7/2004 | Ives et al. | |
| 7,005,653 B1 | 2/2006 | O'Connell et al. | |
| 7,298,869 B1 | 11/2007 | Abernathy | |
| 7,510,555 B2 | 3/2009 | Kanzius | |
| 7,515,948 B1 | 4/2009 | Balberg et al. | |
| 7,894,885 B2 | 2/2011 | Bartal et al. | |
| 2002/0026106 A1 * | 2/2002 | Khalil et al. | 600/310 |
| 2002/0048077 A1 | 4/2002 | Fukumoto | |
| 2002/0073717 A1 | 6/2002 | Dean | |
| 2002/0163735 A1 | 11/2002 | Detlef et al. | |
| 2002/0193678 A1 | 12/2002 | Kruger | |
| 2003/0023152 A1 * | 1/2003 | Abbink et al. | 600/316 |
| 2003/0135110 A1 | 7/2003 | Leussier | |
| 2004/0054268 A1 * | 3/2004 | Esenaliev et al. | 600/322 |
| 2004/0059265 A1 * | 3/2004 | Candy et al. | 601/2 |
| 2004/0067000 A1 | 4/2004 | Bates et al. | |
| 2004/0127783 A1 | 7/2004 | Kruger | |
| 2004/0176805 A1 | 9/2004 | Whelan | |
| 2004/0181153 A1 * | 9/2004 | Hall | 600/448 |
| 2004/0210126 A1 | 10/2004 | Hajaj et al. | |
| 2004/0232321 A1 | 11/2004 | Miles et al. | |
| 2004/0254457 A1 | 12/2004 | vander Weide | |
| 2005/0150309 A1 | 7/2005 | Beard | |
| 2005/0154308 A1 | 7/2005 | Quistgaard et al. | |
| 2005/0175540 A1 * | 8/2005 | Oraevsky et al. | 424/9.5 |
| 2005/0234319 A1 | 10/2005 | Mandelis et al. | |
| 2006/0058685 A1 * | 3/2006 | Fomitchov | A61B 5/0091 600/476 |
| 2006/0064001 A1 * | 3/2006 | Barbour | 600/407 |
| 2006/0084861 A1 | 4/2006 | Blank et al. | |
| 2006/0184042 A1 | 8/2006 | Wang et al. | |
| 2006/0256339 A1 | 11/2006 | Lowney et al. | |
| 2006/0264717 A1 | 11/2006 | Pesach et al. | |
| 2007/0015992 A1 | 1/2007 | Filkins et al. | |
| 2007/0152144 A1 | 7/2007 | Quake | |
| 2007/0197886 A1 | 8/2007 | Naganuma et al. | |
| 2007/0238954 A1 | 10/2007 | White et al. | |
| 2007/0238958 A1 * | 10/2007 | Oraevsky et al. | 600/407 |
| 2007/0274580 A1 | 11/2007 | Ntziachristos et al. | |
| 2008/0071172 A1 | 3/2008 | Bruck et al. | |
| 2008/0118934 A1 | 5/2008 | Gerdes | |
| 2008/0123083 A1 | 5/2008 | Wang et al. | |
| 2008/0173093 A1 | 7/2008 | Wang et al. | |
| 2008/0221647 A1 * | 9/2008 | Chamberland | A61B 5/0095 607/88 |
| 2008/0228073 A1 | 9/2008 | Silverman et al. | |
| 2009/0024038 A1 | 1/2009 | Arnold | |
| 2009/0038375 A1 | 2/2009 | Breuer et al. | |
| 2009/0054763 A1 | 2/2009 | Wang et al. | |
| 2009/0058746 A1 | 3/2009 | Delgado | |
| 2009/0081122 A1 | 3/2009 | Rufenacht et al. | |
| 2009/0192358 A1 | 7/2009 | Jaffer et al. | |
| 2009/0324048 A1 | 12/2009 | Leevy | |
| 2010/0022866 A1 | 1/2010 | Feke et al. | |
| 2010/0078576 A1 | 4/2010 | Ntziachristos et al. | |
| 2010/0249570 A1 | 9/2010 | Carson et al. | |
| 2011/0001975 A1 | 1/2011 | Razansky et al. | |
| 2011/0040176 A1 | 2/2011 | Razansky et al. | |
| 2011/0201914 A1 | 8/2011 | Wang et al. | |
| 2011/0208057 A1 | 8/2011 | Oikawa | |
| 2011/0231160 A1 | 9/2011 | Suzki | |
| 2011/0282192 A1 | 11/2011 | Axelrod et al. | |
| 2011/0301453 A1 | 12/2011 | Ntziachristos et al. | |
| 2011/0306857 A1 | 12/2011 | Razansky et al. | |
| 2011/0306865 A1 | 12/2011 | Thornton et al. | |
| 2012/0029829 A1 | 2/2012 | Li et al. | |
| 2012/0150012 A1 | 6/2012 | Fujimoto et al. | |
| 2012/0238873 A1 | 9/2012 | Lacoste et al. | |
| 2013/0041267 A1 | 2/2013 | Ntziachristos et al. | |
| 2013/0312526 A1 | 11/2013 | Oishi | |
| 2014/0114187 A1 | 4/2014 | Rozenthal et al. | |
| 2014/0163353 A1 | 6/2014 | Razansky et al. | |
| 2014/0198606 A1 | 7/2014 | Morscher et al. | |
| 2014/0221810 A1 | 8/2014 | Kacprowicz | |
| 2014/0336505 A1 | 11/2014 | Ripoll Lorenzo et al. | |
| 2014/0363066 A1 | 12/2014 | Ntziachristos et al. | |

FOREIGN PATENT DOCUMENTS

| | | |
|---|---|---|
| EP | 1 561 424 A1 | 8/2005 |
| EP | 2695893 | 8/2012 |
| IL | 2006/061829 * | 6/2006 |
| JP | 09219563 | 8/1997 |
| JP | 2004351023 | 12/2004 |
| JP | 2007/307007 | 11/2007 |
| JP | 2010125260 | 6/2010 |
| JP | 2012170762 | 9/2012 |
| WO | 2004/068405 A2 | 8/2004 |
| WO | 2006/061829 A1 | 6/2006 |
| WO | 2006/063246 * | 6/2006 |
| WO | WO 2006061829 A1 * | 6/2006 |
| WO | WO 2006063246 A1 * | 6/2006 |
| WO | 2007/084771 A2 | 7/2007 |
| WO | 2007/100937 | 9/2007 |
| WO | WO2007/111669 | 10/2007 |
| WO | WO2008/018082 | 2/2008 |
| WO | 2008/101019 | 8/2008 |
| WO | WO2009/055095 | 4/2009 |
| WO | WO2010/009747 | 1/2010 |
| WO | WO2011/000389 | 1/2011 |
| WO | WO2011/072198 | 6/2011 |
| WO | WO2011/137385 | 11/2011 |
| WO | WO2012/108170 | 8/2012 |
| WO | WO2012/108172 | 8/2012 |
| WO | WO2012/137855 | 10/2012 |
| WO | WO2012/150721 | 11/2012 |
| WO | WO2013/167147 | 11/2013 |
| WO | WO2013/185784 | 12/2013 |
| WO | WO2014/066150 | 5/2014 |

OTHER PUBLICATIONS

L Yin, Q Wang, Q Zhang, and H Jiang, "Tomographic imaging of absolute optical absorption coefficient in turbid media using combined photoacoustic and diffusing light measurements", 2007, Optics Letters, vol. 32, No. 17, pp. 2556-2558.*

Laufer, J. et al., "Quantitative Spatially Resolved Measurement of Tissue Chromosphore Concentrations Using Photoacoustic Spectroscopy: Application to the Measurement of Blood Oxygenation and Haemoglobin Concentration," *Physics in Medicine and Biology*, 2007, vol. 52, pp. 141-168.

Vinegoni, C. et al., "In vivo Imaging of *Drosophila Melanogaster* Pupae with Mesoscopic Fluorescence Tomography," *Nature Methods*, Jan. 2008, vol. 5, No. 1, pp. 45-47 and Supplementary Notes.

(56) References Cited

OTHER PUBLICATIONS

Razansky, D. et al., "Hybrid Photoacoustic Fluorescence Molecular Tomography Using Finite-Element-Based Inversion," *Meical Physics*, Nov. 2007, vol. 34, No. 11, pp. 1-9.
Zacharakis, G. et al., "Volumetric Tomography of Fluorescent Proteins through Small Animals in vivo," *PNAS*, Dec. 20, 2005, vol. 102, No. 51, pp. 18252-18257.
Ash et al., 'Super-Resolution Aperture Scanning Microscope', Nature, vol. 237, Jun. 30, 1972, pp. 510-512.
U.S. Appl. No. 13/381,207, filed Jan. 27, 2012, Razansky et al.
U.S. Appl. No. 13/386,491, filed Apr. 5, 2012, Razansky et al.
U.S. Appl. No. 12/867,265, filed Sep. 20, 2010, Razansky et al.
Larin et al., 'Monitoring of Tissue Coagulation During Thermotherapy Esing Optoacoustic Technique', Journal of Physics D: Applied Physics, 2005, vol. 38, pp. 2645-2653.
'American National Standard for Safe Use of Lasers', Laser Institute of America, ANS1Z136.1, 2007 (revision of ANS1Z136.1 2000).
Chen et al., 'Atomic Decomposition by Basis Pursuit', SIAM Review, 2001, vol. 43 No. 1, pp. 129-159.
Jetzfellner et al., 'Preformance of Interactive Optoacoustic Tomography with Experimental Data', Applied Physics Letters, 2009, vol. 95, pp. 013703.1-013703.3.
Cox et al., 'Gradient-Based Quantitative Photoacoustic Image for Molecular Imaging', Proc of SPIE, 2007, vol. 6437, pp. 643IT.1-643IT.10.
Cox et al., 'Two-Dimensional Quantitative Photoacoustic Image Reconstruction of Absorption Distributions in Scattering Medica by Use of a Simple Iterative Method', Applied Optics, Mar. 10, 2006, vol. 45 No. 8, pp. 1866-1873.
Paltauf et al., 'Iterative Reconstruction Algorithm for Optoacoustic Imaging', J Acoust Soc Am, Oct. 2002,vol. 112 No. 4, pp. 1536-1544.
Jiang et al., 'Spatially Varying Optical and Acoustic Property Reconstruction Using Finite-Element-Based Photoacoustic tomography', J Opt Soc Am, Apr. 2006, Vo. 23 No. 4, pp. 878-888.
Office Action dated Aug. 2, 2013 for U.S. Appl. No. 13/386,491.
Yuan et al., 'Quantitative Photoacoustic Tomography: Recovery of Optical Absorption coefficient Maps of Haterogeneous Media', Applied Physics Letters 88:231101, 2006.
Razansky et al., 'Multispectral Photoacoustic Imaging of Fluorochromes in Small Animals', Optics Letters, vol. 23, No. 19, pp. 2891-2893, Oct. 1, 2007.
Rosenthal et al., 'Quantitative Optoacoustic Signal Extraction Using Sparse Signal Repesentation', IEEE Transactions on Medical Imaging, vol. 28, No. 12, pp. 1997-2006, 2009.
Xu et al., 'Exact Frequency-Domain Reconstruction for Thermoacoustic Tomography—I: Planar Geometry', IEEE Transactions on Medical Imaging, vol. 21, No. 7, pp. 823-828, 2002.
Oraevsky et al., 'Direct Measurement of Laser Fluence Distribution and Optoacoustic Imaging in Heterogeneous Tissues', Proc SPIE 2323, Laser Interactions with Hard and Soft Tissue 11, 37, 1995.
Karabutov et al., 'Optoacoustic Measurement of Optical Properties of Turbid Media', Proc. SPIE vol. 4749, pp. 288-298, 2002.
Razansky et al., 'Multispectral Opto-Acoustic Tomography of Deep-Seated Fluorescent Proteins in Vivo', Nature Photonics, 3, 412-417, 2009.
Schulz et al., 'Experimental Fluorescence Tomography of Tissues with Noncontact Measurements', IEEE Transactions on Medical Imaging, Vo. 23, No. 4, oo 492-500, 2004.
Ripoll et al., 'Free-Space Propagation of Diffuse Light: Theory and Experiments', Phys. Rev, Lett., vol. 91, No. 10, pp. 103901-1-103901-6, 2003.
Zibulevsky et al., 'Blind Source Separation by Sparse Decomposition', ICA, Principle and Practice, Chapter 7, Cambridge, 2001.
Capps, "Near Field or Far Field?", EDN Network, www.ednmag.con Aug. 16, 2001, p. 95-102.
Office Action dated Jun. 3, 2013 for U.S. Appl. No. 12/867,265.

Sugiyama et al., 'Character Pattern Recognition Utilizing Independent Component', Proceedings of the 44th Conference of the Institute of Systems, Control and Information Engineers (ISCIE), p. 457-458, English abstract, 2000.
Taruttis et al., 'Motion Clustering for Deblurring Multispectral Optoaxoustic Tomography Images of the Mouse Heart', Journal of Biopmedical Optics, vol. 17, No. 1, pp. 16009-1 to 16009-4, Jan. 2012.
Taruttis et al., 'Imaging the Small Animal Cardiovascular System in Real-Time with Multispectral Optoacoustic Tomography', Proc of SPIE, vol. 7899, pp. 789913-1 to 789913-8, 2011.
Buehler et al., 'Video Rate Optoacoustic Tomography of Mouse Kidney Perfusion', Optics Letters, vol. 35, No. 14, pp. 2475-2477, Jul. 15, 2010.
Glatz et al., 'Blind Source Unmixing in Multi-Spectral Optoacoustic Tomography', Optics Express, vol. 19, No. 4, pp. 3175-3184, Feb. 14, 2011.
Morscher et al., 'Spectral Unmixing Using Component Analysis in Multispectral Optoacoustic Tomography', Proc SPIE, vol. 8089, 2011.
Morscher et al., 'Blind Spectral Unmixing to Identify Molecular Signatures of Absorbers in Multispectral Optoacoustic Tomography', Proc SPIE, Photons Plus Ultrasound: Imaging and Sensing, vol. 7899, 2011.
Office Action dated Jul. 31, 2014 for U.S. Appl. No. 13/386,491.
Ku et al., 'Thermoacoustic and Photoacoustic Tomography of Thick Biologial Tissues Toward Breast Imaging', Technogy in Cancer Research & Treatment, ISSN 1533-0346, vol. 4, No. 5, dated Oct. 2005.
Office Action dated Jan. 29, 2014 for U.S. Appl. No. 12/867,265.
U.S. Appl. No. 13/399,272, filed Nov. 6, 2014, Kellnberger et al.
Office Action dated Nov. 26, 2014 for U.S. Appl. No. 13/386,491.
Office Action dated Dec. 26, 2014 for U.S. Appl. No. 12/867,265.
Xu et al., 'Universal Back-Projection Algorithm for Photoacoustic Computed Tomography', The American Physical Society,Physical Review, vol. E71, No. 1, pp. 016706, 2005.
Skolnik, Radar Handbook, McGraw Hill, Chapter 8, 2008.
Ye, 'PSTD Method of Thermoacoustic Tomography (TAT) and Related Experimental Investigation', Dissertation, 2009.
Telenkov et al., 'Frequency-Domain Photothermoacoustics: Alternative Imaging Modality of Biological Tissues', Journal of Applied Physics, vol. 105, p. 102029, 2009.
Fan et al., 'Development of a Laser Photothermoacoustic Frequency-Swept System for Subsurface Imaging: Theory and Experiment', J. Acoust. Soc. Am., 116(6), 2004.
Skolnik, Introduction to Radar Systems, Chapter 6.5, McGraw Hill, 2001.
Skolnik, Introduction to Radar Systems, Chapter 11.5, McGraw Hill, 1981.
Rosenthal et al., 'Fast Semi-Analytical Model-Based Acoustic Inversion for Quantitative Optoacoustic Tomography', IEEE Transactions on Medical Imaging, vol. 29, No. 6, Jun. 2010.
Baddour, 'Theory and Analysis of Frequency-Domain Photoacoustic Tomography', J. Acoust. Soc. Am., 123(5), pp. 2577-2590, 2008.
Paltauf et al., 'Three-Dimensional Photoacoustic Tomography Using Acoustic Line Detectors', Soc. Opt. Eng., vol. 6437,pp. 1-10, 2007.
Maslov et al., 'Photoacoustic Imaging of Biological Tissue with Intensity-Modulated Continuous-Wave Laser', Journal of Biomedical Optics, vol. 13, No. 2, pp. 024006, 2008.
Kak et al., 'Principles of Computerized Tomographic Imaging', IEEE Press, Chapters 3 and 6, 1988.
International Preliminary Report dated Dec. 24, 2014 for PCT/EP2012/002466.
Wang, 'Multiscale Photoacoustic Microscopy and Computed Tomography', Nature Photonics, Review Article, 2009.
Zhang et al., 'Collecting Back-Reflected Photons in Photoacoustic Microscopy', Optics Express, vol. 18, No. 2, Jan. 18, 2010.
Wang et al., 'Photoacoustic Tomography: In Vivo Imaging from Organelles to Organs', Science, 335(6075), Mar. 23, 2012.
Yao et al.; 'Photoacoustic Tomography: Fundamentals, Advances and Prospects', contrast Media Mol Imaging 6(5), 2011.

(56) References Cited

OTHER PUBLICATIONS

Li et al., 'Fast-Scanning Reflection-Mode Integrated Photoacoustic and Optical-coherence Microscopy', Proc. of SPIE, vol. 7564, 2010.
Ntziachristos, 'Going Deeper than Microscopy: The Optical Imaging Frontier in Biology', Nature Methods, vol. 7, No. 8, 2010.
Aguirre et al., 'A curved Array Photoacoustic Tomography System for Small Animal Imaging', Proc, SPIE 6437:OV1-OV10, 2007.
Allen et al., 'Dual Wavelength Laser Diode Excitation Source for 2D Photoacoustic Imaging', Proc. SPIE 6437: U1-U9, 2007.
Erpelding et al., 'Three-Dimensional Photoacoustic Imaging with a Clinical Two-Dimensional Matrix Ultrasound Transducer', Photons Plus Ultrasound: Imaging and Sensing, Proc of SPIE, vol. 7899, 2011.
Office Action dated Jan. 28, 2014 for U.S. Appl. No. 13/386,491.
Office Action dated May 7, 2015 for U.S. Appl. No. 13/381,207.
Office Action dated Jul. 7, 2015 for U.S. Appl. No. 13/386,491.
Office Action dated Jul. 14, 2015 for U.S. Appl. No. 14/102,250.
Office Action dated Jul. 14, 2015 for U.S. Appl. No. 14/102,328.
Office Action dated Aug. 30, 2012 for U.S. Appl. No. 12/684,816.
Office Action dated Oct. 2, 2015 for U.S. Appl. No. 12/867,265.
Office Action dated Oct. 6, 2014 for U.S. Appl. No. 13/381,207.
Philips. White Pate for iU22 with X7-2 Probe, 2010, 1 pg, internet. https://web.archive.org/web/20100908015304/http://healthcare.philips.com/main/products/ultrasound/transducers/7x_2.wpd.
Pratt, 'Image Sampling and Reconstruction,' Digital Image Processing: PIKS Scientific Inside by William K. Pratt, pub. Wiley-Interscience; 4 Edition (Feb. 9, 2007); ISBN: 0471767778; Chapter 4.
Song, 'High-Speed Photoacoustic Microscopy in Vivo', Ph.D. Thesis, School of Eng. & Appl. Sci., Washington University, Saint Louis, 133 pgs, 2010.
Viator et al., 'Clinical Testing of a Photoacoustic Probe for Port-Wine Stain Depth Determination', Lasers Surg. Med. 30:141-148, 2002.
U.S. Appl. No. 13/386,491, Final Office Action, Mar. 9, 2016.
U.S. Appl. No. 14/102,250, Final Office Action, Feb. 19, 2016.
U.S. Appl. No. 14/102,328, Final Office Action, Jan. 21, 2016.
U.S. Appl. No. 14/141,773, Non-Final Office Action, Dec. 3, 2015.
U.S. Appl. No. 14/141,773, Final Office Action, Jun. 9, 2016, 49 pages.
Xu, et al., "Time-Domain Reconstruction for Thermoacoustic Tomography in a Spherical Geometry", IEEE Transactions on Medical Imaging vol. 21, No. 7, Jul. 2002, 814-822.
U.S. Appl. No. 14/102,328, Non-Final Office Action, Aug. 26, 2016, 29 pages.
U.S. Appl. No. 13/386,491, Non-Final Office Action, Sep. 23, 2016, 54 pages.
U.S. Appl. No. 14/141,773, Notice of Allowance, Oct. 25, 2016, 21 pages.

\* cited by examiner

QUANTITATIVE MULTI-SPECTRAL OPTO-ACOUSTIC TOMOGRAPHY (MSOT) OF TISSUE BIOMARKERS

RELATED APPLICATIONS

This is a §371 of International Application No. PCT/EP2008/006142, with an international filing date of Jul. 25, 2008 (WO 2010/009747 A1, published Jan. 28, 2010), the subject matter of which is incorporated by reference.

TECHNICAL FIELD

This disclosure relates to a method and a device for quantitative three-dimensional sensing and imaging of target tissue biomarkers, in particular in clinical, small animal and small organism imaging applications using multiple-wavelength illumination.

BACKGROUND

Non-invasive imaging of functional and molecular biomarkers in vivo is an emerging and important capacity in biological discovery, drug discovery and several clinical applications, which goes beyond anatomical imaging and retarded disease identification. Another important prospect of visualizing tissue biomarkers is the ability to examine and quantify treatment responses in vivo by monitoring specific primary molecules or downstream targets. Therapeutic efficacy could then be probed dynamically on timescales of hours to days. This ability is in contrast to the mainstay of today's healthcare with traditionally late end points of drug efficacy, a practice that often impairs prompt revision and exclusion of ineffective treatment strategies with potentially lethal results.

Similarly, while microscopy gives unprecedented insights into biology, it can only penetrate for a few hundred microns in tissues. Therefore the biological in vivo observation is limited by the microscopy penetration limit. Clearly methodologies that can penetrate deeper in tissue and visualize the microscopic contrast or utilize new contrast mechanisms are of immense importance in dynamic observations of biological phenomena, in developmental studies and in the drug discovery process.

Optical functional and molecular mesoscopic and macroscopic imaging of tissues has opened new pathways for study of many pathological processes in vivo. Indeed, optical wavelengths offer great variety of probing mechanisms that can be used for a variety of interrogations, from intrinsic functional information on blood oxygenation to molecular sensing. The use of extrinsically-administered fluorescent optical agents has further advanced the noninvasive photonic imaging by allowing visualization of otherwise invisible cellular and sub-cellular processes. For instance, the use of contrast agents and fluorescent reporters with specificity to proteins and enzymes has shown a high potential to differentiate several diverse disease biomarkers, such as inflammation and tumor progression.

U.S. Pat. No. 6,641,798 discloses tumor-targeted optical contrast agents useful for diagnostic imaging and therapy. The bioconjugates described include cyanine dyes with a variety of bis- and tetrakis (carboxylic acid) homologes. The compounds may be conjugated to bioactive peptides, carbohydrates, hormones, drugs, or other bioactive agents. The small size of the compounds allows more favorable delivery to tumor cells as compared to larger molecular weight imaging agents. These contrast agents are useful for diagnostic imaging and therapy, in endoscopic applications for the detection of tumors and other abnormalities, for localized therapy, for opto-acoustic tumor imaging, detection and therapy, and for sonofluorescence tumor imaging, detection and therapy. Fluorescence molecular tomography (FMT) is also capable of sensing picomole to femtomole quantities of fluorochromes in deep tissues at macroscopic scale, i.e., in whole animals with millimeter resolution. The technique shares tomographic principles with diffuse optical tomography and utilizes multi-projection illumination, combined with mathematical models that describe photon propagation in tissues, to reconstruct three-dimensional tomographic images of fluorochrome concentration.

U.S. Pat. No. 6,615,063 describes a fluorescence-mediated molecular tomographic imaging system, designed to detect near-infrared fluorescence activation in deep tissues. The system can use targeted fluorescent molecular probes or highly sensitive activable fluorescence molecular probes. Such probes add molecular specificity and yield high fluorescence contrast, to allow early detection and molecular target assessment of diseased tissue, such as cancers, in vivo.

Recently, tomographic imaging of tissues using opto-acoustics (photo-acoustics) has also demonstrated the ability to achieve penetration depths from several millimeters up to centimeters range with ultrasonic resolution. Opto-acoustic imaging relies on ultrasonic detection of opto-acoustically induced signals following absorption of pulsed light. The amplitude of the generated broadband ultrasound waves reflects local optical absorption properties of tissue. Since scattering of ultrasonic waves in biological tissues is extremely weak, as compared to that of light, biomedical opto-acoustic imaging combines high optical absorption contrast with good spatial resolution limited only by ultrasonic diffraction. Photo-acoustic imaging was proven efficient in imaging vascular trees, tumor angiogenesis, blood oxygenation monitoring, as well as sensitive to tissue chromophores, light-absorbing nanoparticles and dyes, and chromogenic assays.

For instance, U.S. Pat. No. 5,840,023 teaches a laser opto-acoustic imaging system, which utilizes time-resolved measurement of profiles of laser-induced transient pressure (acoustic) waves. The pressure waves are emitted by acoustic sources preferentially generated in absorbing tissues of diagnostic interest. This technique allows visualization of absorbed light distribution in turbid, layered and heterogeneous tissues irradiated by laser pulses in vivo. The laser opto-acoustic tomography can be used for the characterization of structure and properties of normal tissue, and for the detection of tissue pathological changes. The optical heterogeneities that can be imaged with the laser opto-acoustic imaging system include abnormal tissues such as tumors, injured tissues, blood vessels and other layered tissues. Further, three dimensional images of organs and portions of organs can be obtained.

Therefore, multi-spectral detection is often applied, as a means to better discriminate spectral signatures of various objects of interest. For example, U.S. Pat. No. 6,208,749 discloses a system for multi-spectral imaging of skin tissue that enables automatic characterization of the condition of a region of interest of the skin, based on direct digital imaging of that region or the digitization of its color photographic slides, when illuminating by appropriately filtered light. Parameters related to the texture, asymmetry, blotchiness and border irregularities are automatically estimated. The region of interest is automatically characterized by the digital processor, based on those parameters. The region of interest may include a skin lesion, in which case the characterization of the lesion as malignant or benign is enabled.

In U.S. Pat. No. 6,760,609, a method for determining an arterial blood oxygen saturation level by measuring the light transmittance through tissue of light of a first wavelength and a second wavelength is suggested. A steady-state component of the measured light transmission is used to select an appropriate calibration curve. A pulsatile component of the measured light transmission is used to determine the arterial blood oxygen saturation level using the selected calibration curves of oxy- and deoxy-hemoglobin spectral signatures. An oximetry system is further provided wherein a plurality of light transmission measurements are used to determine a blood oxygen saturation level.

In opto-acoustic spectroscopy, multi-wavelength methods were previously applied for differentiating blood chromophores (J. Laufer et al., "Phys. Med. Biol." vol. 52, p. 141-168, 2007, U.S. Pat. No. 7,298,869).

U.S. Pat. No. 6,498,942 also discloses an opto-acoustic apparatus which includes a radiation source of pulsed radiation and a probe having a front face to be placed in close proximity to or in contact with a tissue site of an animal body. The probe further includes a plurality of optical fibers terminating at the surface of the front face of the probe and connected at their other end to a pulsed laser. The front face of the probe also has mounted therein or thereon a transducer for detecting an acoustic response from blood in the tissue site to the radiation pulses connected to a processing unit which converts the transducer signal into a measure of venous blood oxygenation. Another method, disclosed in US 2004/0127783, was suggested for imaging of dye markers by generating images with and without dye stimulation using two wavelengths (inside and outside the frequency band of fluorescence of the dye) and combining those for image enhancement.

A limitation of the above illumination techniques is that when operating with optically complex structures, such as tissue, the resulting images are a combined effect of the targeted chromophore and other native tissue chromophores. This complexity is particularly important in molecular imaging applications where molecular marker has to be resolved in the presence of many other non-specific tissue absorbers. In addition, opto-acoustic (or: photo-acoustic) observations so far have been limited to utilizing mono-directional homogenous illuminations, operating on the assumption that a similarly homogeneous illumination will occur as light propagates in tissue.

For example, WO 2007/084771 describes a method that delivers illumination which establishes "a homogeneous distribution of an energy fluence within any given plane or slice inside the body . . . ." Such illumination field is very difficult to achieve in practice, since tissue heterogeneity is not known and can impose significant variations of light intensity at any given plane inside tissue. When cylindrical objects are considered, such as the mouse torso, the conversion of mono-directional illumination in polar co-ordinates results in the utilization of multiple illumination points, arranges so that light is directed towards the center of the object, in the longitudinal sense. In this case, to simplify the illumination and detection arrangements, it is required that the tissue of investigation is surrounded by water or a similar fluid.

It could therefore be helpful to provide an improved imaging method, in particular for clinical and preclinical imaging or laboratory search purposes, which is capable of avoiding disadvantages of conventional techniques. In particular, it could be helpful to provide an imaging method which enables three-dimensional localization in tissues and quantification of molecular probes with increased precision. Furthermore, it could be helpful to provide an improved imaging device, in particular, being adapted for conducting the imaging method. The method and device are to be provided yielding, in particular, practical implementations and highly accurate discrimination of tissue biomarkers in vivo.

SUMMARY

We provide a method of multi-spectral opto-acoustic tomography (MSOT) imaging of a target tissue including a target tissue biomarker, including illuminating the target tissue with an illumination device emitting at least one pulsed illumination pattern at several illumination wavelengths, detecting pressure signals from the target tissue biomarker with a detector device, wherein the pressure signals being produced in the target tissue are in response to the illumination, and reconstructing a quantitative tomographic image of a distribution of the target tissue biomarker in the target tissue, wherein the pressure signals are analyzed using a photon propagation model which depends on an illuminating light fluence in the target tissue and on the illumination wavelengths, at least one spectral processing scheme, and an inversion scheme providing the tomographic image.

We also provide an imaging device adapted for multi-spectral opto-acoustic tomography (MSOT) imaging a target tissue including a target tissue biomarker, including an illumination device adapted for illuminating the target tissue with at least one pulsed illumination pattern at several illumination wavelengths that are absorbed by the target tissue biomarker, a detector device that detects pressure signals produced from the target tissue biomarker in the target tissue in response to the illumination, and a reconstruction device that reconstructs a quantitative tomographic image of a distribution of the target tissue biomarker in the target tissue, whereas the reconstruction device includes a processor adapted for calculating a photon propagation model which depends on the light pattern that illuminates the target tissue and on the illumination wavelengths, a processor adapted for implementing a spectral processing scheme, and a processor adapted for implementing an inversion scheme providing the tomographic image.

BRIEF DESCRIPTION OF THE DRAWINGS

Further details and advantages are described in the following with reference to the attached drawings, which show in.

DETAILED DESCRIPTION

This disclosure is based on the general technical teaching of quantitative three-dimensional sensing and imaging of tissue biomarkers, in particular in clinical, small animal and small organism imaging applications using multiple-wavelength illumination while accounting for photon propagation in tissue to achieve accurate knowledge of the multi-spectral photon excitation field, which in turn generates acoustic pressure waves. The method combines pressure wave measurements together with a photon propagation model and multi-spectral information to achieve three-dimensional biomarker images of unprecedented image quality, fidelity and overall accuracy.

We provide a method of multi-spectral opto-acoustic tomography (MSOT) imaging a target tissue including a target tissue biomarker, comprising the steps of illuminating the target tissue with at least one pulsed illumination pattern at several illumination wavelengths that are absorbed by the target tissue biomarker, detecting pressure signals (in particular acoustic signals) from the target tissue biomarker, wherein the pressure signals being produced by the target tissue biomarker in the target tissue in response to the illumination, and reconstructing a quantitative tomographic image of a distribution of the target tissue biomarker in the target tissue, wherein the pressure signals are analyzed using a photon propagation model, which depends on a light pattern illuminating the target tissue and on the illumination wavelengths, a spectral processing scheme, and an inversion scheme providing the tomographic image.

We also provide an imaging device, which is adapted for multi-spectral opto-acoustic tomography (MSOT) imaging of the target tissue including the target tissue biomarker. The imaging device comprises an illumination device being configured for illuminating the target tissue with at least one pulsed illumination pattern including several illumination wavelengths absorbed by the target tissue biomarker, a detector device being configured for detecting pressure signals being produced from the target tissue biomarker in the target tissue in response to the illumination, and a reconstruction device reconstructing a quantitative tomographic image of a distribution of the target tissue biomarker in the target tissue. The reconstruction device includes a processor calculating a photon propagation model, a processor implementing a spectral processing scheme, and a processor implementing an inversion scheme providing the tomographic image. The image constructed represents a spatial distribution of at least one biomarker in the target tissue.

Preferably, the reconstruction device is adapted for applying inverse methods and spectral processing to build the image of a vessel, in particular blood vessel, like a coronary or a carotid artery, wherein the image represents a spatial distribution of the biomarker at a wall of the vessel.

Advantageously, we combine wavelength-tuned mathematical photon modeling in tissue together with a multi-spectral processing technique to improve functional and molecular imaging across different imaging scales. Three-dimensional biomarker images of unprecedented image quality, fidelity and overall accuracy are achieved. Furthermore, we provide the multi-spectral illumination biomarker reporter imaging device that can be built with a small form factor to detect tissue biomarkers. Advantageously, this device can be applied to imaging molecular markers in biological samples and in clinical applications. Particular advantageous applications comprise resolving fluorescent proteins and/or extrinsically-administered chromogenic or fluorescent dyes in clinical inflammatory and cardiovascular applications and in other living biological samples.

To detect a biomarker in the target tissue with optical methods, light is delivered locally at the area of the biomarker (or biomarker reporter). However, as light propagates in tissue, intrinsic tissue absorption and overall light propagation characteristics alter the propagation pattern, by creating a heterogeneous deposition of energy in the various tissue elements which is also wavelength-dependent. Thus it becomes challenging to isolate the contribution of the biomarker on the detected signal.

As outlined in the above background section, multi-spectral methods, including opto-acoustic methods, have been utilized in functional measurements to resolve tissue attenuation in selected wavelengths, and derive the concentrations of oxy- and deoxy-hemoglobin, cytochrome oxidase and possibly other tissue chromophores and externally administered dyes. However the conventional implementations assume simple photon propagation patterns. A common conventional assumption is that plane wave illumination will result in a plane-wise uniform photon distribution in tissue, which is a very crude assumption that has so far resulted in only superficial blood vessel images.

Contrary to the conventional techniques, we developed a method to perform opto-acoustic imaging of tissue biomarker reporter, offering high-fidelity, true three-dimensional and quantitative imaging not only of superficial but also of deeper seated contrast. Compared to techniques that have been applied to resolve common chromophores, a particularly advantageous feature is the integration of multi-spectral measurements together with a wavelength-depended model of photon propagation in tissue to provide an accurate estimate of photon propagation in tissue. This approach is essential for providing accurate opto-acoustic images and is particularly important in clinical imaging, whereas the generic assumptions of conventional photoacoustic imaging (uniform illumination, immersion in matching fluids) are not practical. It is thus one feature to provide quantitative information of photon distribution in the target tissue.

The correction for light distribution can be applied to the reconstructed images of biomarker distribution. Alternatively, the correction for light distribution is directly applied to the detected raw opto-acoustic signals. In this case, the final quantified optical absorption image will be reconstructed (by, e.g., back-projection) using already normalized raw opto-acoustic recordings.

Imaging molecular marker distribution in real tissues by means of opto-acoustics may further present an additional challenge. First, in-vivo optical absorption contrast can reach up to two orders of magnitude at some wavelengths. In particular, some areas with high blood content are very absorptive, making the marker hard to distinguish from the highly absorbing background. Images obtained from real tissues will usually represent an added contribution of absorption not only by molecular markers of interest but also by numerous tissue chromophores, like melanin, red blood cells and the like that may also considerably change their optical absorption with the wavelength, especially in the visible. Some of these chromophores may have a significant cross-talk with the extinction/absorption spectra of the biomarker of interest, which might further complicate its detection over background.

Therefore, another important feature is the application of a multi-wavelength spectral matching procedure, incorporating an a-priori known or measured spectra of the marker as well as the mostly important intrinsic tissue constituents. This is crucial for reaching the ability of quantification of molecular marker accumulation in highly heterogeneous tissues. Advantageously, the spectral matching procedure can be applied during various phases of the image formation, e.g., during the calculation of the photon propagation model, and/or during the image reconstruction from the opto-acoustic data by back-projection.

Multi-wavelength excitation is considered particularly advantageous for molecular imaging applications since it does not require "baseline" measurements, i.e., measurements before the administration of the molecular marker. Therefore molecular marker with long accumulation or activation times, or the modulation of intrinsic tissue molecular markers, such as fluorescent proteins can be accurately detected with high sensitivity. Conversely, since illumination at multiple wavelengths is provided, the method is even applicable in imaging dynamic phenomena, such as hemo-dynamics or the circulation of non-specific dyes of varying concentration over small period of times (such as ICG), whereas preferably correction steps are applied based on prior knowledge on kinetics.

We enable molecular imaging with powerful potential applications due to its superior spatial resolution in the opto-acoustic mode, the use of non-ionizing radiation and the increased availability of molecular markers that can impact detection sensitivity, such as numerous targeted or activatable fluorochromes, fluorescence proteins or chromophoric substances.

As compared to most pure chromophores, having relatively broadband optical absorption characteristics, many fluorochromes, e.g., Alexa or Cy-based dyes, ICG, fluorescent proteins (GFP, RFP), exhibit sharp resonances in the vicinity of their peak excitation spectra, making them convenient candidates for highly sensitive multi-wavelength imaging. Also, some fluorochromes, especially in the near-infrared, possess relatively high molar extinction coefficients in excess of $10^5$ $M^{-1}$ $cm^{-1}$ in conjunction with low quantum yield (acting in favor of opto-acoustic signal generation). Thus, even though more specific pure chromogenic molecular markers may be developed, imaging of readily available fluorochromes can be achieved at physiologically useful concentrations even in the presence of highly absorbing tissue chromophores. Acquisition at an even larger number of wavelengths could lead to independently resolving multiple absorbers, markers and fluorochromes at the expense of longer acquisition times.

Preferably, the pressure signals are detected with an acoustic detector device. Alternatively, the pressure signals can be obtained with optical measurements sensing variations of the target tissue surface. Operating with optical detection, the method can be utilized in free-space mode and complete projection mode for complete-body small animal imaging (G. Zacharakis et al., PNAS 102 (51): pp. 18252-18257, 2005) or mesoscopic imaging (C. Vinegoni, C. Pitsouli, D. Razansky, et al., NATURE METHODS 5(1), 2008) with varying resolution depending on the dimensions of the object imaged.

Implementations in tomographic reflection or transillumination can be further utilized for clinical imaging in detecting through several centimeters of breast tissue in, e.g., transillumination mode or at a depth of 4 cm to 5 cm in reflectance mode, for example, in detecting cardiovascular or neurological disease. Operating with acoustic detection this method can be applied with increased (ultrasound like) resolution in similar applications and geometrical implantations, typically, however, through matching media for acoustic detection, for example, matching fluids or gels.

Preferably, the illumination pattern includes at least two spectrally distinct wavelength ranges in a time-shared fashion. Preferably, the illuminating step comprises illuminating the target tissue with at least two pulse-shaped illumination patterns, which are subsequently directed onto the target tissue. Particularly preferred, the illumination patterns are provided with a time interval below 1 s, preferably below 1 ms, down to 10 µs depending on size of the imaged object and its distance from the point where pressure measurement are recorded. The minimal possible interval has to be selected such that the pressure signals originating from all the points in the imaged area have to be measured before launching the next illumination pulse. In this way, distortions of the pressure signals collected with the distinct wavelength ranges can be avoided.

Further preferably, the at least two spectrally distinct wavelength ranges of the illumination pattern include at least two wavelengths with different absorptions of the target biomarker, resp. The distinct wavelength ranges cover at least two spectral absorption areas, in which the target tissue biomarker has different absorption values. Preferably, the biomarker molecules have a variation in the absorbing spectrum within a range below 100 nm, particularly preferred below 70 nm, e.g., in the range of 20 nm to 50 nm.

The photon propagation model considered can account not only for absorption heterogeneity in the target tissue but also for scattering heterogeneity if necessary. According to further preferred features, the photon propagation model is preferably calculated on the basis of at least one of the following approaches.

First, the photon propagation model can be calculated (constructed) using a solution of a photon transport equation, adapted to a geometry of illumination in the target tissue and detection of the pressure signals. Second, the photon propagation model can be calculated using an empiric model of photon transport in the target tissue.

With the first and second approach, distribution of the illuminating light fluence can be calculated according to the concrete geometric conditions of the target tissue. The photon propagation model depends on changes of the illumination light wave front due to structures in the target tissue providing an improved analysis of the pressure signals. For example, as we previously showcased (D. Razansky and V. Ntziachristos, MEDICAL PHYSICS 34 (11): pp. 4293-4301, 2007), the light fluence throughout the sample can be calculated by solving the diffusion equation based on the absorption map and boundary conditions derived by opto-acoustic image at the previous step. As another example, for most clinical applications, where photons will penetrate for several millimeters to centimeters in tissue, a diffusion model may be appropriate. Correspondingly for small animal and in particular for mesoscopic imaging, whereas mesoscopic implies the 0 cm to 1 cm sized tissues, a solution of a more accurate model of photon propagation, including numerical or analytical solutions of the transport equations, will generally be preferred.

Third, a model incorporating incident photon distribution and/or the illumination pattern can be used for calculating the photon propagation model. This variant is preferred if the illumination pattern is provided with a predetermined geometric distribution of photon density. As an example, if the illumination pattern is provided at the output of an optical fiber, the photon propagation model is calculated on the basis of a point-shaped incident photon distribution and a spherical propagation of the illumination light. With another example of a rectangular illumination array, the incident photon distribution and/or illumination pattern introduced into the photon propagation model is adapted accordingly.

With a fourth approach, the detected pressure signals and/or opto-acoustic images produced at any reconstruction stage can be used for calculating the photon propagation model. In this advantageous case, no assumptions on the illumination field are needed, so that this method can operate in any illumination set-up, from operating a handheld scanner with multiple illumination areas, to intravascular imaging. This is one of the particularly preferred features. While most conventional systems follow guidelines that are directed towards utilizing matching fluids and certain optical arrangements that allow for homogenous illumination of tissue, this example is independent of the particulars of the geometrical setup of the source and the detector. In addition, the use of multi-spectral imaging approach allows to resolve important tissue biomarkers in a functional and molecular imaging sense over nonspecific absorption background.

With other words, preferably, instead of indirect photon propagation modeling, the photon fluence in tissue can be directly extracted from the opto-acoustic data. As outlined with further details below, the opto-acoustic signals represent a product between the local light fluence and the local absorption coefficient. In most practical cases, it can be assumed that the fluence exhibits much slower spatial dependence as compared to more rapid absorption coefficient variations. This fact can be utilized to effectively decompose these two contributions using blind source separation methods, e.g., by fitting the combined opto-acoustic response $\psi^k(\lambda)=U^k(\lambda)\mu^k(\lambda)$ into sparse representation dictionary that contains two or more bases with distinct spatial characteristics. The particular advantage of this methodology is its independence from the particular experimental geometry and measurement conditions.

The above approaches for calculating the photon propagation model can be combined for further improving the image reconstruction.

The inversion step of the method is provided for reconstructing the, e.g., three-dimensional distribution of the biomarker from a set of measured pressure signals. The specific inversion scheme will differ in each case depending on particular geometrical and physical characteristics and spatial distribution of the detection elements used. Typically, the inversion can be done by backprojecting the raw or spectrally processed signals recorded by each point detector into the virtual imaged volume and summarizing over all the detector positions (projections).

The inversion may also include normalization of the raw opto-acoustic signals or image by the photon propagation model (light distribution model). Accordingly, preferably, the inversion scheme combines the photon propagation model and an acoustic propagation model in a tomographic reconstruction to yield the quantitative tomographic image.

The inversion scheme preferably combines the photon propagation model and/or the acoustic propagation model in an iterative fashion. In many practical implementations, especially in small animal and clinical applications, optical absorption maps reconstructed opto-acoustically can be fed into the photon propagation model in an iterative fashion, to further improve the prediction of photon propagation and the resulting opto-acoustic reconstructions.

As a further advantage, the spectral processing scheme can be conducted during various phases of the image reconstruction. In particular, preferably, the spectral processing scheme includes an integration into the inversion scheme, a processing step on the collected pressure signal data, and/or a processing step on the reconstructed image data.

Due to the improved processing of the pressure signal data, in particular in dependence on the photon propagation model and the spectral model, we offer new options of designing the imaging device, which is adapted for implementing the imaging method. According to a first advantageous variant, both the illumination device and the detector device, in particular illumination light output elements and sensor elements thereof, can be integrated into an integral component (so called: measuring head unit). Using the measuring head unit provides essential advantages in terms of conducting the imaging and detecting steps. Positioning the illumination and detector devices is essentially facilitated as the measuring head unit simply can be positioned in contact with a target tissue component to be investigated. In particular, the measuring head unit can be positioned on an inner surface of the target tissue, e.g., in a hollow organ or a vessel, like a blood vessel, or on an outer surface of the target tissue, e.g., on the outer skin. Accordingly, with a particular advantageous variant, at least one of the illumination device and the detector device of the imaging device is included in an endoscopic, laparoscopic or interstitial device.

As a particular advantage, the measuring head unit can be provided as a hand-held device for non-invasive or endoscopic and intravascular applications. Furthermore, the measuring head unit can be used without a matching fluid between the measuring head unit and the target tissue. Advantageously, the contact of the measuring head unit with the target tissue is sufficient for introducing the illumination pattern and for collecting the pressure signals.

Advantageously, the measuring head unit can be designed in dependence on particular requirements of application. Preferably, the measuring head unit comprises an array of illumination elements and sensor elements. The array of illumination and sensor elements comprises an arrangement of the illumination and sensor elements with distances relative to each other on a contact surface of the measuring head unit which, depending on the application, is a plane contact surface or a curved contact surface.

The array of illumination and sensor elements provides the illumination pattern (geometric pattern of illumination light to be introduced into the target tissue) and a geometric pattern of sensor elements collecting the pressure signals for tomographic image reconstruction. Particularly preferably, the array of illumination and sensor elements comprises at least one line-shaped arrangement of the illumination elements and at least one line-shaped arrangement of the sensor elements, and/or a matrix-shaped arrangement of the illumination and sensor elements with an alternating distribution thereof.

According to a second variant of the imaging device, the illumination device and the detector device, in particular, the illumination elements and sensor elements thereof, can be provided as separate components. In this case, advantages in terms of adapting the geometry and position of the illumination and detector devices relative to the target tissue can be obtained. As a first example, both the illumination and detector devices are commonly arranged on an outer surface or an inner surface of the target tissue as noted above. Preferably, one of the illumination and detector devices is arranged in the target tissue, in particular, in contact with an inner surface thereof, while the other of the illumination and detector devices is arranged outside the target tissue, in particular in contact with the outer surface thereof. If the illumination device is arranged in the target tissue, e.g., in a vessel or in a subcutaneous condition directly in the tissue, the illumination of the target tissue can be improved, while with the detector device arranged on the outer surface of the target tissue, the collection of the pressure signals can be facilitated.

In the opposite case, the illumination device can be arranged on the outer surface of the target tissue, so that the positioning of the illumination elements relative to the tissue to be investigated can be improved. In this case, the detector device, e.g., as a part of an endoscopic device can be arranged in the target tissue, like, e.g., in a hollow organ or a vessel of the target tissue or if necessary even in a subcutaneous condition.

Another advantage of the array of illumination elements is obtained if the illumination elements are configured for providing illumination light with different projection directions relative to the target tissue. Preferably, the illumination elements are arranged such that at least two different diffusive projection directions are obtained. Illuminating the target tissue with at least two different projection directions has the particular advantage of providing a complex illumination light field which facilitates the inversion of the collected pressure signals to the reconstructed target tissue image.

The detection of tissue biomarkers can be accomplished by resolving intrinsic tissue chromophores and fluorochromes or utilize biomarker reporters, i.e., at least one endogenous reporter such as a fluorescent protein or an extrinsically administered probe with specificity to certain tissue biomarkers. Reporters that absorb light such as fluorochromes and fluorescent dyes or fluorescent conjugates, chromophoric agents and substrates or nano-particle agents based on noble (gold, silver and the like) or other metals are preferred. Advantageously, existing molecular markers can be resolved with the method, including fluorescent probes, absorbing targeted or encapsulated nano-particles and fluorescent proteins. Further preferably, the target tissue includes a light-absorbing reporter to target the biomarker. This allows applications in basic biological imaging as well as in pre-clinical imaging and clinical applications.

As preferred examples, the light-absorbing reporter includes at least one of fluorescent or chromophoric molecules, e.g., AlexaFluor, fluorescent proteins, e.g., GFP, noble-metal-containing particles, e.g., gold nanoparticles, super-paramagnetic particles, e.g., iron-oxide nanoparticles (SPIO), carbon particles, and activatable substrates, e.g., X-gal.

Accordingly, the method operates with a plurality of substances that absorb light. Preferably, imaging performance is increased by selecting predetermined biomarker reporters with a characteristic pattern in their absorption spectrum, for example, a steep absorption change. The term "steep change in the absorption spectrum" refers to an absorption property according to which at least 80% of the peak extinction (or absorption) of the reporter is lost within spectral window of less than 100 nm, particularly preferred less than 50 nm, like, e.g., 20 nm (as it is the case with the fluorescent molecule AlexaFluor750) in the window 750 nm to 770 nm.

Of particular general interest is imaging near-infrared fluorescent markers since their extinction/absorption spectrum exhibits a steep drop in the spectral window above 630 nm compared to the smooth absorption variation of the spectra of common tissue chromophores in this region. In this way, intrinsic tissue contrast can be readily suppressed with a multi-wavelength approach, yielding highly sensitive cancerve imaging of fluorochrome distribution in tissue obtained by spectral matching of opto-acoustic images acquired at several different adjacent wavelengths. In addition, multi-spectral imaging can be employed to resolve multiple absorbers/fluorochromes in tissues and, as mentioned above, the overall method can be further improved by more accurately considering the relative background absorption attenuation of tissue at each of the wavelengths used.

Preferably, the device is used for imaging tissue of small animals, tissue of mesoscopic size, i.e., tissue having a typical dimension in the range of 100 µm to 5 cm in particular from 0.5 mm to 1 cm, or tissue or a tissue component of a human body (or an animal body having a size comparable with a human body). Preferably, the imaging allows to obtain information on the basis of which subsequently a diagnosis can be prepared. The imaging of target tissue biomarkers in particular provides information for diagnosing a cancer disease, a cardiovascular disease, in particular including arteriosclerotic plaque, an inflammatory disease. Alternatively, the imaging allows to obtain an information on a disease state and/or the development of a disease treatment.

A particular preferred implementation is described herein that can image fluorescent proteins in biological specimen such as insects, worms, fish and mice, rabbits, pigs, non-invasively. A particular implementation is also described to detect atherosclerotic biomarkers in cardiovascular disease. However, different approaches in cancer, immunology, neurodegenerative disease and the like can be foreseen.

The quantitative tomographic image is provided as the result of the method. Additionally, the image can be at least one of being displayed by a display device, stored in a computer storage device, recorded with a recording device, like, e.g., a printer or other image output device, and provided as input data for an image processing method.

With specific reference now to the drawings in detail, it is stressed that the particulars shown are by way of example and for purposes of illustrative discussion of preferred forms only, and are presented in the cause of providing what is believed to be the most useful and readily understood description of the principles and conceptual aspects. In this regard, no attempt is made to show structural details in more detail than is necessary for a fundamental understanding, the description taker with the drawings making apparent to those skilled in the art how the several forms may be embodied in practice. As used herein, an element or step recited in the singular and proceeded with the word "a" or "an" should be understood as not excluding plural elements or steps, unless such exclusion is explicitly recited. In the description of the figures, like numbers refer to like parts. The drawings are generally not to scale. For clarity, non-essential elements were omitted from some of the drawings. Some optional elements may be drawn in dashed lines.

1. Preferred Features

Figure 1:
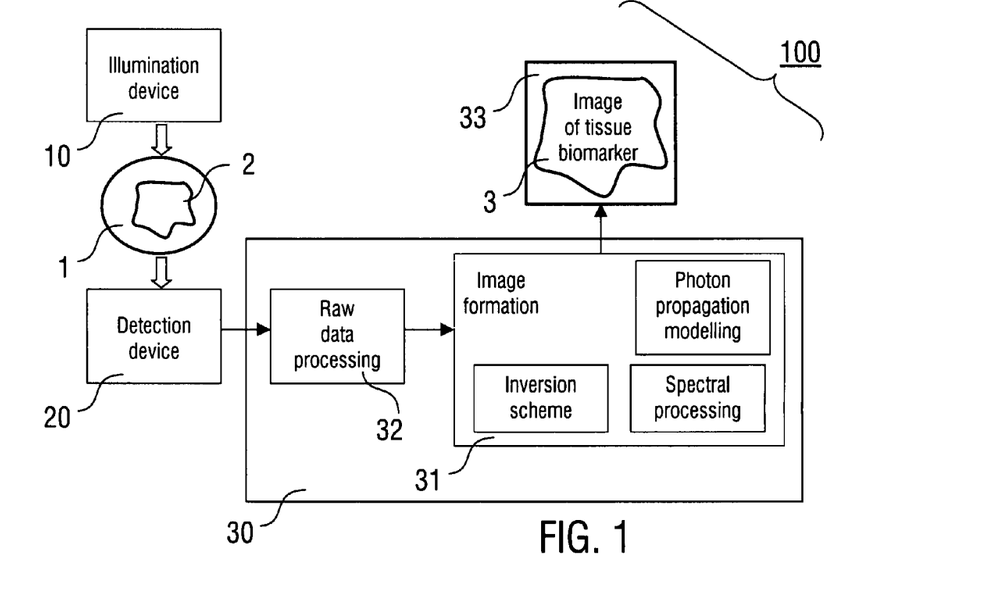
FIG. 1: a schematic representation of examples of target tissue biomarker imaging.

The essential components of the imaging method and imaging device are illustrated in FIG. 1. The imaging device 100 comprises the illumination device 10, the detector device 20 and the reconstruction device 30. The illumination device 10 is arranged for introducing illumination light with a predetermined illumination pattern into the target tissue 1 including a distribution of biomarker 2 to be imaged.

The illumination device 10 can be embodied by various light sources as outlined below. The particular light source used is selected in dependence on the requirements of the application. Typically, the illumination device 10 comprises a light source, like a laser source or a light-emitting diode (LD), and a light guiding device, like an optical fiber transmitting the illumination light from the light source to an output or a contact surface of the illumination device 10. Furthermore, the illumination device 10 is preferably adapted for emitting at least one pulsed illumination pattern at several illumination wavelengths in the far red or near-infrared wavelength range, i.e., preferably with wavelengths above 630 nm.

The detector device 20 is adapted for sensing pressure signals from the target tissue 1, which are produced by the biomarker 2 in the target tissue 1 in response to the illumination. Typically, the detector device 20 is an acoustic detector device including at least one movable detector element and/or a plurality (array) of detector elements. The latter is known, e.g., from ultrasonic imaging techniques. Alternatively, the pressure signals can be collected with an optical detector device immersed in a matching liquid or noncontactly by sensing surface variations of the target tissue with optical means, e.g., by an optical interferometric set-up.

The reconstruction device 30 generally is adapted for reconstructing a quantitative tomographic image of the biomarker 2 in the target tissue 1. The reconstruction device 30 includes at least one processor 31, which is adapted for calculating the photon propagation model, implementing the spectral processing scheme and implementing the inversion scheme for providing the tomographic image. Additionally, a processor 32 adapted for raw data processing can be provided. Processors 31 and 32 can be implemented in a common circuitry. Alternatively, the above functions of the processor 31 can be fulfilled by a plurality of separate processor elements included in the reconstruction device 30. Each processor can be implemented with a microprocessor programmed for fulfilling the particular function thereof.

The reconstruction device 30 is connected with an output device 33, which is adapted for providing the reconstructed tomographic image for further processing or application. In particular, the output device 33 includes at least one of a display device, like, e.g., a display of a computer, a storage device, like, e.g., a storage medium in a computer, and a recording device, like, e.g., a printer.

The imaging method is conducted with the imaging device 100 of FIG. 1 as outlined in the following. Illumination light is beamed upon the imaged region of interest in tissue 1 using the illumination device 10. Preferably, a pulsed illumination at multiple wavelengths is emitted at one or more positions, or angles, into the tissue 1 in the visible and/or near-infrared spectral range. This ability to utilize light forming multiple projections (positions or angles) facilitates the provision of the imaging device as a handheld scanner, or intravascular scanner (see below). Preferably, the duration of individual pulses lie in the nanosecond range (i.e., below 100 ns, particularly preferred below 10 ns) with an interval of at least 10 to 100 μs.

A broadband acoustic radiation is induced in tissue 1 following the instantaneous temperature elevation caused by absorption of the above pulses in tissue 1. The magnitude of the induced acoustic waves is proportional to the local light fluence, optical absorption coefficient and thermoelastic properties of the object.

The pressure signals (acoustic waves, in particular sound) generated in response to the illumination is subsequently detected by the detector device 20. The induced response is collected by translating acoustic detector elements around the tissue 1 or, alternatively, by placing an array of stationary detector elements in the vicinity of the tissue 1.

The optical absorption can be then reconstructed by back-projecting the detected pressure signals into the virtual imaged volume or by various Radon transformations. When assuming constant thermoelastic properties, selected tissue biomarkers 2 can be quantitatively reconstructed based on a distinct absorption spectrum, by solving the composite problem of photon propagation in the tissue 1, which is either wavelength dependent or operates under a simplification that all wavelengths considered propagate in a medium with the same or similar optical properties.

Preprocessing of raw data with the processor 32 may include basic filtering and denoising. The image formation processor 31 applies the inversion scheme appropriate for the particular illumination and detection configuration. It also applies the spectral processing step responsible for differentiation of biomarker from the background absorption in tissue 1 and photon propagation modeling step intended for biomarker image quantification. In the image formation phase, the order of the inversion, photon propagation modeling and spectral processing steps can be changed based on the particular implementation and application needs. As a result, an image 3 of the tissue biomarker 2 of interest is produced.

The specific inversion scheme will differ in each case depending on particular geometrical and physical characteristics and spatial distribution of the detection elements used. For example, in case a phased-array of acoustic detector elements is used, the images can be formed in the real-time by incorporating into the inversion process simple ultrasound beam forming algorithms.

The basic result of the inversion can be presented in a form of image/s 3 representing local optical absorption coefficient of tissue 1.

2. Theoretical Considerations

In practice, the detected opto-acoustic response does not directly provide the local absorption coefficient $\mu(\lambda)$ but the reconstructed image of absorbed energy density $\psi^k(\lambda)$ rather represents a combination of the absorption coefficient $\mu(\lambda)$ and optical fluence $U^k(\lambda)$ in the sample, i.e., $\psi^k(\lambda)=U^k(\lambda)\mu^k(\lambda)$. Due to strong optical attenuation and heterogeneity of biological tissues, the fluence cannot usually be assumed constant throughout the region of interest. Yet, only the absorption coefficient itself can provide the relevant quantitative information on biomarker distribution. Therefore, the ability to quantify the actual distribution of the marker within the sample heavily relies on the initial accuracy of reconstruction of the optical absorption map at each wavelength that is to be deconvolved from the light fluence distribution.

Opto-Acoustic Inversion

A broadband acoustic radiation is induced in tissue following the instantaneous temperature elevation caused by absorption of short pulses of light energy in matter. The magnitude of the induced acoustic waves is proportional to the local energy density, optical absorption coefficient, and thermoelastic properties of the object. Their spectrum, in turn, is mainly dependent upon the spatial frequency of energy deposition variations and duration of the emitted pulses. For pulse durations in the ns range, a biologically relevant opto-acoustic spectrum will be of ultrawideband nature with useful information contained between several tens of kHz and several tens of MHz, depending on size and spatial distribution of optical absorption variations within the imaged object.

Preserving the correct shape of the detected response is important for the correct quantification of the resulting images. Since it may be difficult to effectively implement such a broadband detection, a preferred way to restore the initial tissue response is to deconvolve the recorded signal from the frequency response of the detector. Alternatively, ultrawideband detection approaches may be used, such as optical interferometric approaches based on detection of surface movements or mechanical oscillations in optically resonant elements, e.g., Fabry-Perot films, ring resonators, or etalons.

The inversion is provided for reconstructing the, e.g., three-dimensional distribution of the biomarker from the collected ultrasonic pressures $p(\vec{r}',t)$ by backprojecting the raw or spectrally processed signals. The specific inversion scheme will differ in each case depending on particular geometrical and physical characteristics and spatial distribution of the detection elements used. For example, in case a phased-array of detector is used, the images can be formed in the real-time by using the simple ultrasound beam forming algorithms.

Generally, under conditions of heat confinement, i.e., when the light energy pulse is short enough so that the thermal diffusion is insignificant during the pulse, the spatio-temporal dependence between opto-acoustically induced pressure $p(\vec{r},t)$, absorbed energy density $\psi(\vec{r},t)$ (in J/m$^3$) and local temperature elevation $T(\vec{r},t)$ can be expressed as $$\nabla^2 p(\vec{r},t) - \frac{1}{v_s^2}\frac{\partial^2 p(\vec{r},t)}{\partial t^2} = -\rho_m \beta \frac{\partial^2 T(\vec{r},t)}{\partial t^2} = -\frac{\beta}{C}\frac{\partial \psi(\vec{r},t)}{\partial t} \quad (1)$$

where $v_s$, $\rho_m$, $\beta$, and C are the corresponding speed of sound, mass density, isobaric volume expansion, and specific heat of the medium, all are in general spatially and frequency dependent.

In practice, the thermal confinement conditions are fulfilled for excitation pulse durations less then 1 μs. When for instance a point-shaped detector element of small diameter (e.g., below 1 mm) is placed in the position $\vec{r}'$, at the first approximation it will sense an integrated pressure wave, which is the solution of (1), namely, $$p(\vec{r}',t) = -\frac{\beta}{4\pi C}\int_V \frac{\partial \psi(\vec{r},t')}{\partial t'}\frac{d^3\vec{r}}{|\vec{r}-\vec{r}'|}\bigg|_{t'=t/v_c} \quad (2)$$

The basic result of the inversion step can be presented in a form of image/s representing local deposition of tissue biomarker.

Photon Propagation Modelling

Tissue biomarker imaging is based on reconstruction of the local optical absorption. However, as already mentioned, raw opto-acoustic data do not represent the absorption coefficient directly but rather a combination of the absorption coefficient and optical fluence in the sample. Preferably, a quantitative description of photon propagation (fluence rate) in tissue based on known models of light propagation in tissues is utilized to decompose optical absorption from fluence.

The fluence throughout the region of interest can be calculated using light transport equation in diffuse media. One of the preferred approximations, the diffusion equation, takes the form $$-D\nabla^2 U(\vec{r}) + \mu_a U(\vec{r}) = q_0 \quad (3)$$

where $D = 1/[3(\mu_s' + \mu_a)]$ is the diffusion coefficients of the medium ($\mu_a$ and $\mu_s'$ are the absorption and reduced scattering coefficient, respectively) and $q_0(\vec{r})$ is the source distribution. For solving this differential equation, spatially-varying optical properties of the medium $\mu_a$ and $\mu_s'$ as well as the spatial distribution and strength of the source element on the right-hand-side have to be known. In complex geometries, the light diffusion can be calculated with Eq. (3) by using finite-element method approaches.

It must be noted that the light diffusion approximation is only valid in macroscopic objects with size many times larger than the mean-free path (MFP) in tissue, normally corresponding to objects larger than 10 mm. For smaller object, mesoscopic approximations to light transport equation are applied. One of the most accurate yet computationally extensive approached in this case will be applying Monte-Carlo simulations of light transport. Yet, some simple analytical approximations, like fermi function, can be effectively applied, as we have demonstrated in C. Vinegoni, C. Pitsouli, D. Razansky, et al., NATURE METHODS 5(1), 2008.

Spectral Processing

We provide an efficient method for imaging of molecular marker of interest by suppressing intrinsic tissue contrast with the multi-wavelength approach. This yields highly sensitive imaging of molecular marker distribution in tissue obtained by spectral matching of images acquired at several different wavelengths. While the simplest qualitative version of this operation can be achieved by image subtraction at two wavelengths, three- and overall multi-wavelength imaging will further suppress the background signals. This processing can occur in several stages, an efficient one being the simultaneous inversion of spectral data so that all information is accurately accounted for.

Preferably, simplified computation, however, will utilize the following general quantification formula for the reconstructed amount (concentration) of the molecular marker of interest $C^k$ on a per pixel basis:

$$C^k = \min_{c^k}\sum_{\lambda=\lambda_1}^{\lambda_N}[\psi^k(\lambda) - c^k\varepsilon(\lambda)]^2 \quad (4)$$

where $C^k$ is the reconstructed amount (concentration) of the molecular marker of interest on a per pixel/voxel basis, N is the total number of illuminating wavelengths, $\psi^k(\lambda)$ is the reconstructed absorption in pixel/voxel k, $c^k$ and $\varepsilon(\lambda)$ are the concentration and wavelength-dependent molar absorptivity of the marker, respectively. We note that the wavelength-dependent absorption coefficient $\mu(\lambda)$ in each pixel/voxel will be written in a conventional form as $$\mu(\lambda) = \sum_{m=1}^{M} c_m^k \varepsilon_m(\lambda), \quad (5)$$

where M is the total number of wavelength-dependent markers and tissue chromophores considered in the reconstruction procedure. The procedure in Eq. (4) will then include minimization over a set of concentrations $c_m^k$ (m = 1, ..., M).

Alternatively, it can be assumed that every pixel k in the opto-acoustic image may represent a combined contribution of the molecular and other background tissue chromophores. For every imaged wavelength $\lambda$, this can be written in the form of linear equation:

$$\mu_a^k(\lambda) = \alpha_{MM}(\lambda)c_{MM}^k + \alpha_1(\lambda)c_1^k + \alpha_2(\lambda)c_2^k + \ldots,$$

where $\mu_a^k(\lambda)$ is the reconstructed wavelength-dependent absorption in pixel k, $\alpha_{MM}(\lambda)$ and $\alpha_1(\lambda)$, $\alpha_2(\lambda)$, ... are the molar extinction spectra of the molecular marker and the background chromophores, and $c_{MM}^k$ and $c_1^k$, $c_2^k$, ... are the corresponding concentrations. Using the measured absorption values and the known spectra for the seven wavelength, the concentration $c_{MM}^k$ of the molecular marker/s and the background chromophores can be subsequently reconstructed from the above linear equations on a per-pixel basis using linear regression method.

The preferred methodology for achieving molecular marker differentiation resides in including spectral information into the inversion mode using a single-step or a two step method.

The single-step method comprises inverting a tomographic equation simultaneously for the different wavelengths employed, therefore simultaneously accounting for 1) the photon attenuation as a function of depth (distance from the source), 2) the detection process and 3) the wavelength dependence of the measurements.

The dual step method pre-processes the raw data using a spectral matching or decomposition algorithm and then utilizes one processed measurement as the input to an inversion code that accounts only for 1) the photon attenuation as a function of depth (distance from the source) and 2) the detection process. An alternative two-step method can be implemented by reconstructed images at different wavelengths and then processing the resulting images on a pixel by pixel basis.

Image Formation

Figure 2:
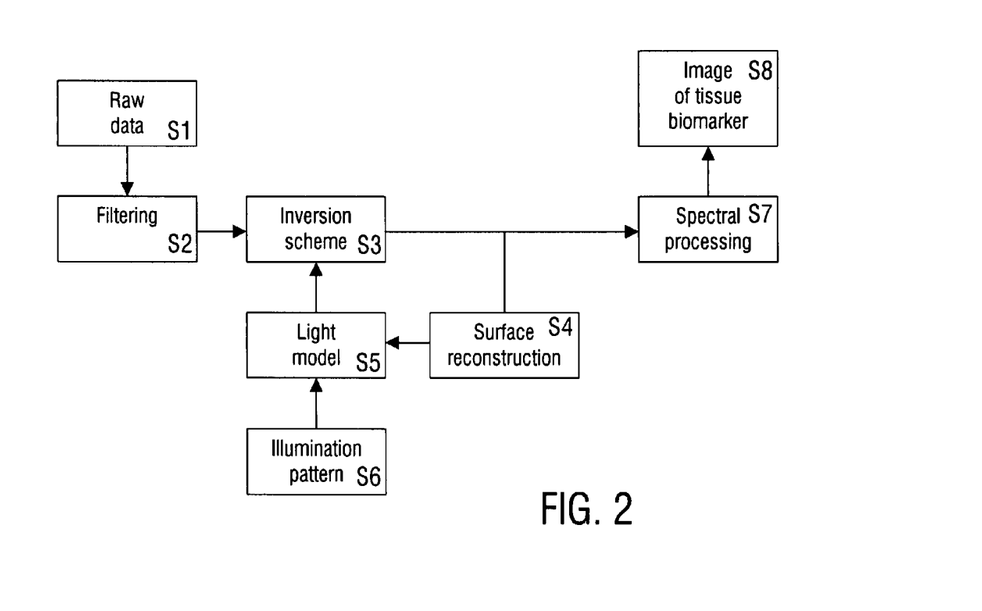
FIG. 2: a schematic flowchart illustrating features of preferred examples of the imaging method.

An example of image formation process is shown in FIG. 2. The raw opto-acoustic recordings (step S1) are initially filtered (step S2) and sent into the inversion scheme (step S3). The resulting initial reconstructed image is then processed to extract the geometry (boundary, inner or outer surface) of the imaged target tissue (step S4). This is provided for the subsequent light distribution modelling (step S5) in the tissue that is calculated using (step S6) a-priori known pattern of the light incident upon the tissue. The process is repeated in an iterative manner, where, at each step, the inversion scheme normalizes the reconstructed image by the calculated light distribution, which is also iteratively improving. For biomarker visualization (step S8), the images are spectrally processed (step S7) for background absorption elimination.

3. Further Applications

There is a wealth of applications for the method. While not limited only to the bio-medical field, the application of the technique to medical and biological imaging is an important direction.

3.1 Biological Imaging

Figure 3:
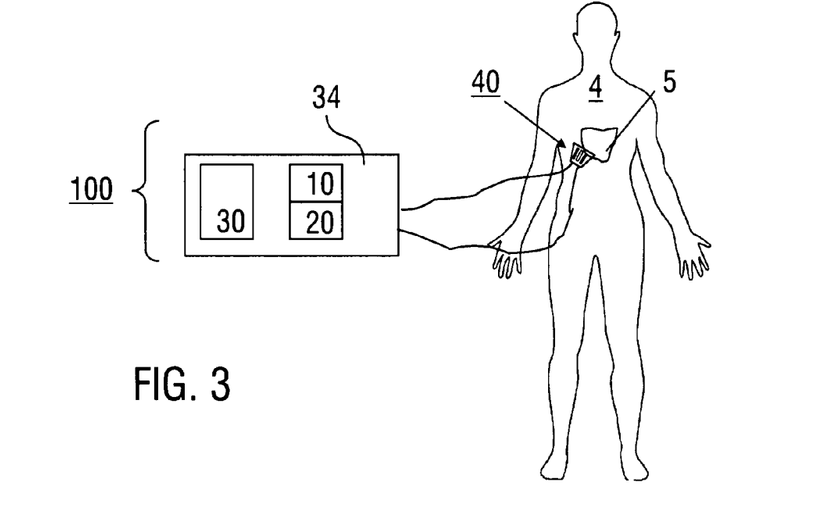
FIGS. 3 to 5: schematic illustrations of a measuring head unit of an imaging device.

FIG. 3 schematically illustrates an example whereas for imaging a part of a human proband 4 (e.g., patient), e.g., the target tissue 1 comprising an organ 5. The imaging device 100 comprises the illumination device 10, the detector device 20 and the reconstruction device 30, which are integrated into a common casing 34 and a measuring head 40 being connected with the illumination and detector devices 10, 20 via optical fibers and electrical cables.

Figure 5:
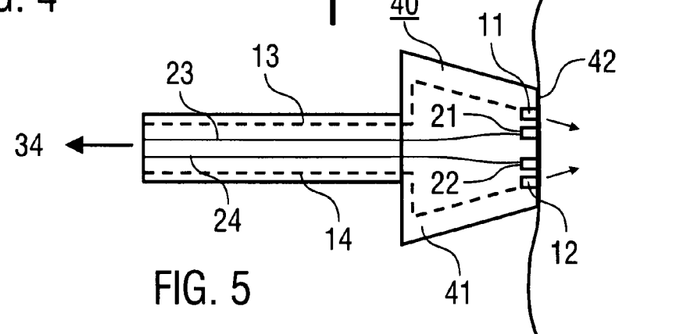
Figure 6:
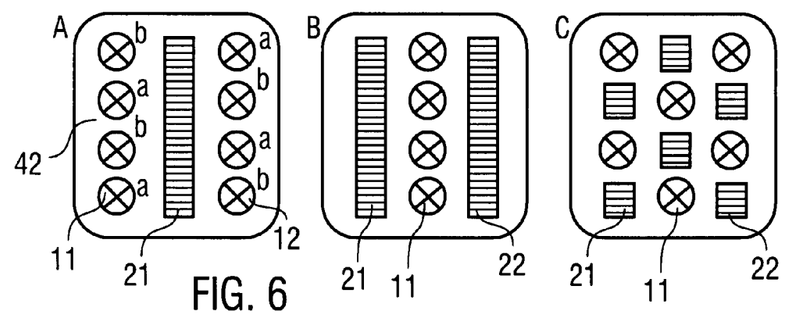
FIG. 6: an illustration of an array of illumination and sensor elements of an imaging device.

The measuring head 40 can include separate components of illumination and sensor elements as illustrated below in FIG. 4. Alternatively, the measuring head comprises an integral measuring head unit including the illumination elements and sensor elements in a common casing as outlined with further details below (FIGS. 5 and 6).

Preferably, an agent is injected intravenously or locally to the proband 4, and targets areas or processes of interest. The measuring head unit 40 is brought in contact with the tissue so that illumination light is coupled into it and pressure signals can be sensed. The collected pressure data are processed and presented in the form of two- or three-dimensional image on a monitor.

An application example includes the administration of fluorescence emitting agents that are preferentially uptaken by macrophages. Image of their absorption yields areas of increased inflammation as in the case of image atherosclerotic plaque, in the carotids or other vessels. Similarly targeted absorbing particles can show information on targeted molecules such as peptides, receptors and the like.

Figure 4:
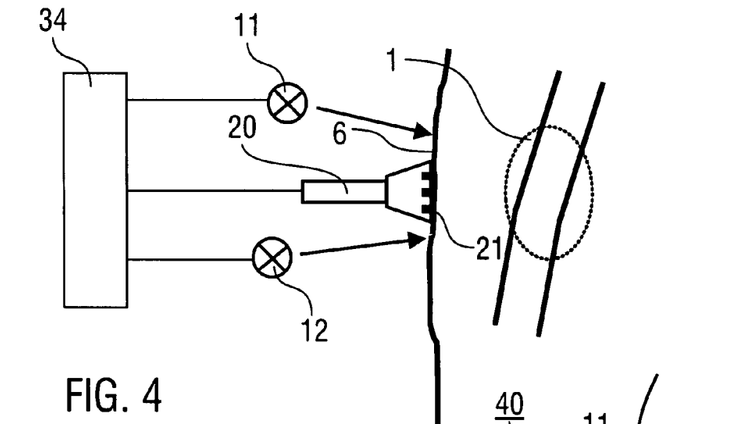

FIG. 4 schematically illustrates adjustment of the imaging device 100 relative to the target tissue 1 to be investigated. The illumination device comprises at least two illumination elements 11, 12, which are arranged with a distance relative to each other, e.g., 15 mm. The distance of the illumination elements 11, 12 from the outer surface 6 (e.g., skin) of the target tissue 1 comprises, e.g., 20 mm. Alternatively, the illumination elements 11, 12 can be arranged in contact with the outer surface 6. The illumination elements 11, 12 comprise, e.g., LED's with a predetermined emission characteristic defining the projection direction towards the target tissue 1. Alternatively, the illumination elements 11, 12 comprise the output ends of optical fibers being connected with a laser source of the imaging device 100, e.g., in the casing 34.

The detector device 20 comprises an array of detector elements 21 being embedded in a surface (contact surface) of the detector device 20. The contact surface is adapted to be brought into contact to the outer surface 6 of the target tissue 1. The detector device 20 comprises, e.g., a sound sensor as it is known from conventional ultrasound imaging devices.

Alternatively, the illumination and sensor elements 11, 12, 21 are integrated within a common measuring head unit 40 and are illustrated in FIGS. 5 and 6. The measuring head unit 40 comprises a casing body 41, into which the illumination elements 11, 12 and the sensor elements 21, 22 are embedded. The illumination and sensor elements 11, 12, 21, 22 are integrated into the contact surface 42 of the measuring head unit 40. Elements 11, 12, 21, 22 are respectively connected via optical fibers 13, 14 and electrical wires 23, 24 with the associated parts of the illumination and detector devices 10, 20 integrated in the casing 34 (see, e.g., FIG. 3).

FIGS. 6A, 6B and 6C illustrate examples characterized by different distributions of the illumination and sensor elements 11, 12, 21, 22 in the contact surface 42 of the measuring head unit 40. According to FIG. 6A, line-shaped arrangements are provided with two outer rows of illumination elements 11, 12 (e.g., LED's or output ends of optical fibers) and a central row of sensor elements 21 (acoustical sound sensors). FIG. 6B illustrates the opposite geometry with a central row of illumination elements 11 and outer rows of sensor elements 21, 22. FIG. 6C shows a matrix arrangement of the elements 11, 12, 21, 22.

The illumination elements 11, 12 are configured for illuminating the target tissue with at least one pulsed illumination pattern at several illumination wavelengths. As an example, for providing two distinct wavelength ranges, a first group of illumination elements 11 (e.g., indicated with "a") is adapted for emitting illumination light with wavelengths in the range of 610 nm to 650 nm, while a second group (indicated with "b") is adapted for emitting wavelengths in the range of 670 nm to 730 nm. For emitting a larger number of wavelength ranges, a third or more groups are provided.

It is emphasized that the number of illumination and detector elements shown in FIG. 6 is selected for illustrative proposes only. In practice, the number of elements can be selected in dependence on the illumination and sound detection requirements.

Figure 7:
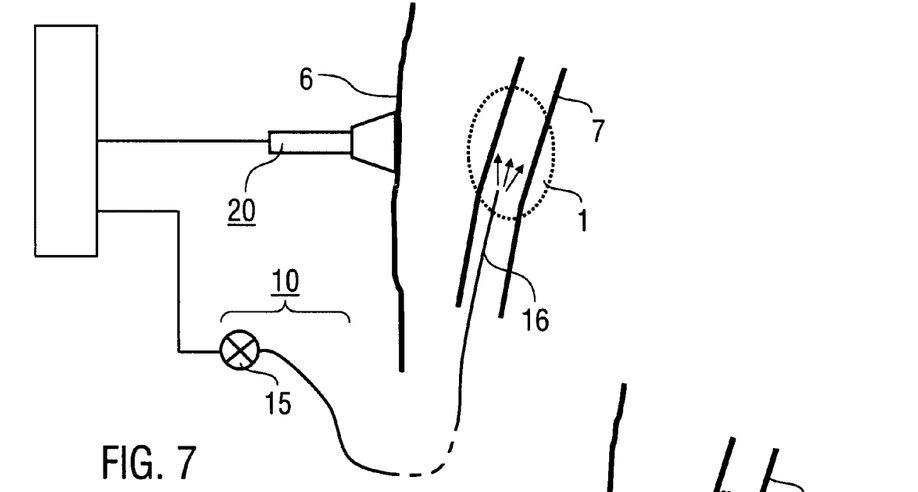
FIGS. 7 to 9: schematic illustrations of alternative examples of the imaging method and device.
Figure 8:
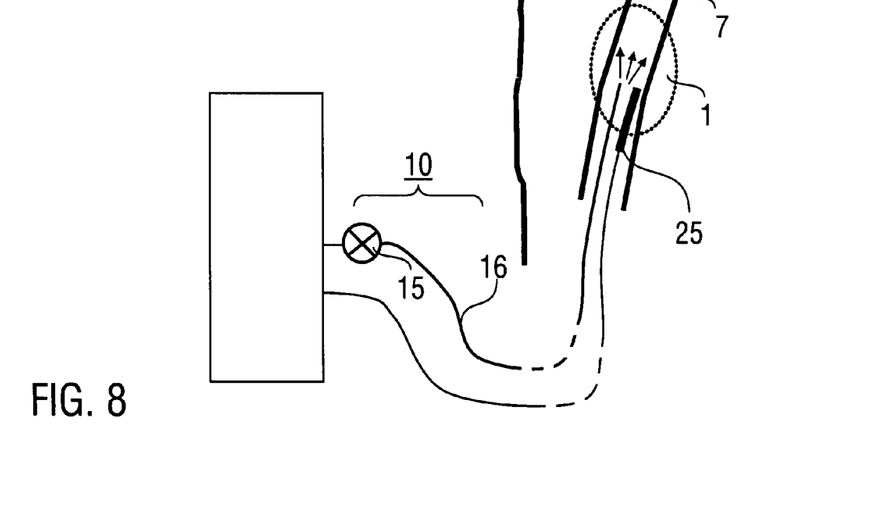
Figure 9:
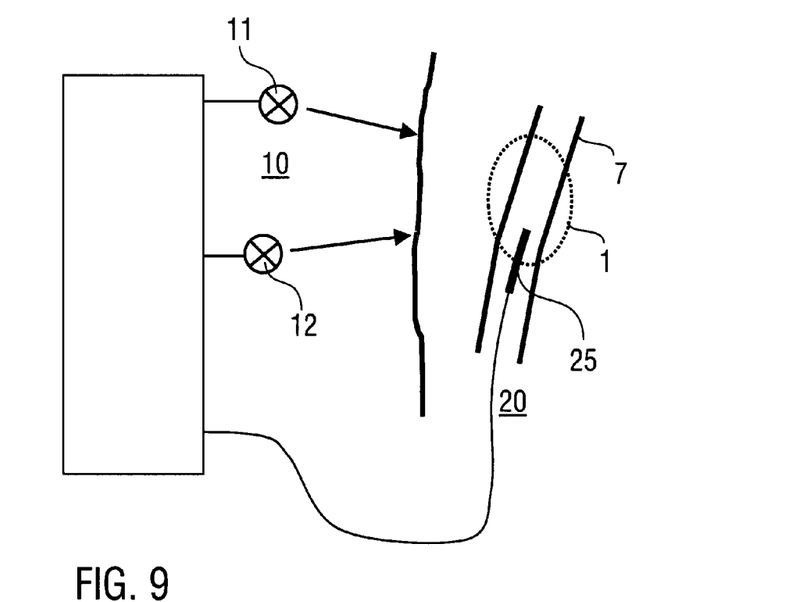

FIGS. 7 to 9 illustrate further examples, wherein illumination and detector elements are used that are separated from each other. As an example, imaging a target tissue 1 including a blood vessel 7 is illustrated.

According to FIG. 7, the illumination device 10 comprises a light source 15 and an optical fiber 16, that is introduced into the blood vessel 7 to the position of the target tissue 1 to be imaged. The detector device 20 comprises an array of detector elements, which is adapted to be brought into contact with the outer surface 6 of the target tissue 1, e.g., skin of a human body. In operation, illumination light patterns with distinct wavelength ranges are emitted via the optical fiber 16 onto the inner surface of the blood vessel 1. Pressure signals created by absorbing biomarkers within tissue 1 are sensed with the detector device 20.

For example, if Cy5.5 dye is used for bio-marker targeting with peak absorption at 670 nm, the multi-spectral illumination device might include diode-laser-based illumination device emitting light at 7 distinct wavelengths, namely, 610, 630, 650, 670, 690, 710, and 730 nm, that cover areas of both high and low absorption of the dye to ease on the subsequent multi-spectral processing and suppression of background absorption signals.

According to FIG. 8, both the optical fiber 16 of the illumination device 10 and the sensor element 25 of the detector device 20 are arranged in the blood vessel in the target tissue 1. Both components can be integrated in an endoscopic device (not shown).

According to FIG. 9, the illumination elements 11, 12 of the illumination device 10 are arranged outside the target tissue, while the detector element 25 of the detector device 20 is provided in the vessel within the target tissue 1.

Figure 10:
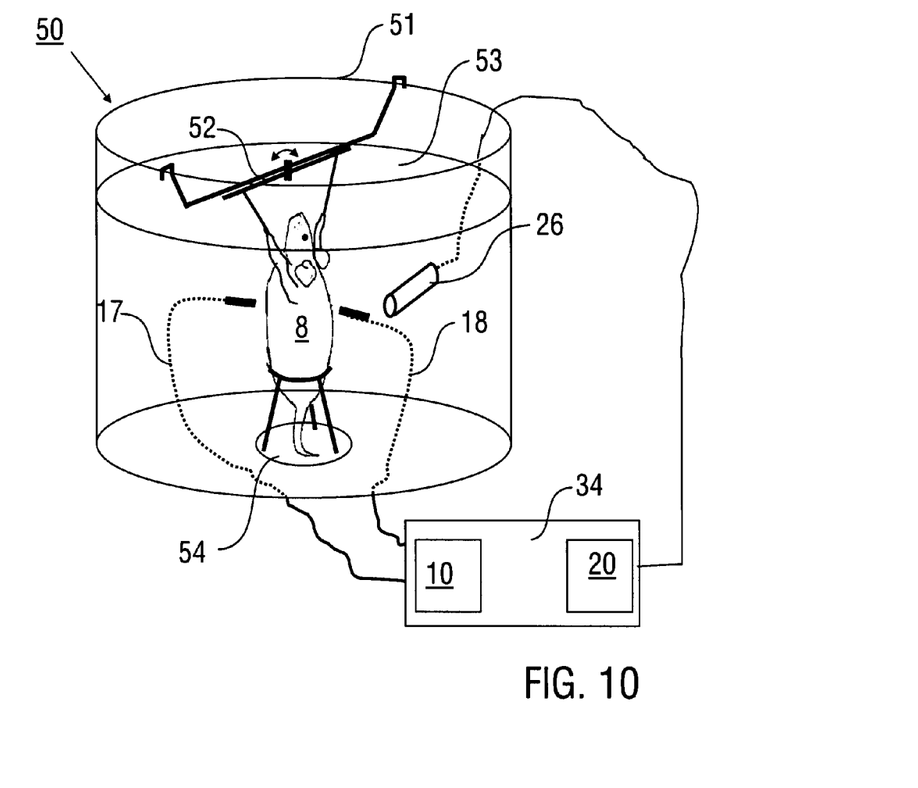
FIG. 10: an experimental set-up for imaging small animals in a laboratory experiment.

FIG. 10 illustrates a preferred application of the technique in biomedical imaging of mesoscopic-size objects and small animals, like mice or other rodents, flies, fishes, worms, animal embryos. A container device 50 is provided, which comprises a tank 51 and holding elements 52, 54 which are adapted for positioning components of the imaging device 100. The tank 51 contains a matching fluid 53, e.g., water or oil. The object to be investigated (living mouse 8) is positioned on the lower part 54 of the rod or plate shaped holding element.

The illumination device 10 and the detector device 20 are partially integrated in a casing 34 (see above, FIG. 3), that is are arranged outside the container device 50. The illumination device 10 comprises a pulsed laser source whose light is directed to the mouse 8 from two opposite directions 17,18 by, e.g., using optical mirrors or fibers. The detector device 20 comprises an array 26 of acoustic detector elements. The detector device 20 is arranged in the neighborhood of the holding element 52 with the mouse 8. Advantageously, there are no particular restrictions with regard to the position of the detector device 20. The preferred location, however, will be as close as possible to the object to obtain measurements with high signal-to-noise ratios. For implementing the above image reconstruction, it is only necessary to have an information on the location of the array of detector elements relative to the object (mouse 8).

The example schematically illustrated in FIG. 10 is not restricted to the investigation of small animals. Alternatively, other biological objects can be imaged, e.g., human beings or larger animals or parts thereof. As an example, tank 51 can be adapted for accommodating a part of a human patient instead of the mouse 8.

3.2 Clinical Imaging

Areas of preferred clinical applications include imaging of cardiovascular disease, cancer, inflammation and neuro-degenerative disease, to name a few examples. Imaging of natural states such as growth and aging are also contemplated. As a particular advantage, the near-field imaging can be conducted without using a matching fluid between the near-field source device and the object to be investigated, thus essentially facilitating the clinical applications.

Another application example includes imaging of the effect of treatment, via drugs, radiation or chemotherapy, by similarly administrating absorbing particles in the body and monitoring their relative update or targeting over time.

In other examples, the same detection can be achieved by portable devices, or endoscopic devices inserted into body cavities or through invasive procedures by operatively inserting the device into the tissue.

It is appreciated that certain features, which are, for clarity, described in the context of separate examples, may also be provided in combination in a single example. Conversely, various features, which are, for brevity, described in the context of a single example, may also be provided separately or in any suitable sub-combination. Although the device has been described in conjunction with specific examples thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into this specification, to the same extent as if each individual publication, patent or patent application was specifically and individually indicated to be incorporated herein by reference. In addition, citation or identification of any reference in this application shall not be construed as an admission that such reference is available as prior art.

The invention claimed is:

1. A method of multi-spectral opto-acoustic tomography (MSOT) imaging of a target tissue including at least one target tissue biomarker, the method comprising:

illuminating the target tissue using several different illumination wavelengths;

detecting pressure signals from the at least one target tissue biomarker with a detector, wherein the pressure signals are produced in the target tissue in response to said illuminating the target tissue; and reconstructing a quantitative tomographic image of a spatial distribution of a concentration of the at least one target tissue biomarker in the target tissue, said reconstructing of the quantitative tomographic image comprising:

applying an inversion scheme to the pressure signals to provide a reconstructed optoacoustic image $\psi^k(\lambda)$ at each of the different illumination wavelengths;

separating contributions of a light fluence $U^k(\lambda)$ and an absorption coefficient $\mu^k(\lambda)$ to the reconstructed image $\psi^k(\lambda)$ at each of the illumination wavelengths using a blind source separation method, whereby the absorption coefficient $\mu^k(\lambda)$ is obtained at each of the illumination wavelengths; and using at least one spectral processing scheme to resolve the at least one target tissue biomarker, wherein the spectral processing scheme processes, on a pixel-bypixel basis, the absorption coefficient $\mu^k(\lambda)$ obtained at each of the illumination wavelengths to resolve the spatial distribution of the concentration of the at least one target tissue biomarker.

2. The imaging method according to claim 1, wherein said illuminating the target tissue comprises providing an illumination pattern that includes at least two spectrally distinct wavelength ranges in a time-shared fashion.

3. The imaging method according to claim 1, wherein said reconstructing of the quantitative tomographic image comprises analyzing one or more of the pressure signals or the reconstructed optoacoustic images $\psi^k(\lambda)$ via a photon propagation model that is calculated using at least one of the following:
   a solution of a photon transport equation, adapted to a geometry of illumination of the target tissue;
   an empiric model of photon transport in the target tissue;
   a model incorporating incident photon distribution and/or the illumination pattern; and/or
   the detected pressure signals and/or opto-acoustic images produced at any reconstruction stage.

4. The imaging method according to claim 1, wherein the inversion scheme combines a photon propagation model and an acoustic propagation model in a tomographic reconstruction to yield the quantitative tomographic image.

5. The imaging method according to claim 4, wherein the inversion scheme combines the photon propagation model and the acoustic propagation model in an iterative fashion.

6. The imaging method according to claim 1, wherein the spectral processing scheme includes at least one of the following:
   integration thereof into the inversion scheme;
   a processing step on the collected data; and
   a processing step on the reconstructed data.

7. The imaging method according to claim 1, wherein one or more of the following applies:
   said illuminating the target tissue is achieved via an illumination device that comprises a light source or a light guide that transmits light from a light source, the illumination device and the detector being integrated in a common measuring head, wherein the illuminating and detecting steps include positioning the measuring head in contact with a target tissue component or matching fluid;
   the illumination device is arranged in the target tissue and the detector is arranged in contact with an outer surface of the target tissue or matching fluid;
   the detector is arranged in the target tissue and the illumination device is arranged outside or in contact with an outer surface of the target tissue;
   the illumination device and the detector are arranged in contact with an outer surface of a target tissue; or
   the detection device measures opto-acoustically induced pressure signals in a non-contact manner.

8. The imaging method according to claim 1, wherein said illuminating the target tissue is achieved via an illumination device that comprises a light source or a light guide that transmits light from a light source, and wherein the illumination device and the detector are arranged inside a blood vessel using an intravascular catheter; or a measuring head that comprises each of the illumination device and the detector is a hand-held device.

9. The imaging method according to claim 1, wherein the target tissue includes a light-absorbing reporter to target the biomarker.

10. The imaging method of claim 9, wherein the light absorbing reporter includes at least one of:
    fluorescent or chromophoric molecules;
    fluorescent proteins;
    noble-metal-containing particles;
    super-paramagnetic particles;
    carbon particles; or
    activatable substrates.

11. The imaging method of claim 9, wherein the light-absorbing reporter includes a steep change in its absorption spectrum.

12. The imaging method of claim 11, wherein the illumination wavelengths include at least two wavelengths that are differentially absorbed by the target bio-marker.

13. The imaging method according to claim 1, wherein the target tissue biomarker targets at least one of:
    a cancer disease;
    a cardiovascular disease, in particular including atherosclerotic plaque;
    inflammatory disease;
    an aspect of disease for diagnostic purposes;
    an aspect of disease state; or
    an aspect of disease treatment.

14. The imaging method according to claim 1, wherein the target tissue includes at least one of:
    tissue of a small animal;
    tissue of mesoscopic size; or
    tissue of at least one human organ.

15. An imaging device for multi-spectral opto-acoustic tomography (MSOT) imaging of a target tissue including at least one target tissue biomarker, the imaging device comprising:
    an illumination device that comprises a light source or a light guide that transmits light from a light source, the illumination device being configured to illuminate the target tissue with at least one pulsed illumination pattern at several different illumination wavelengths that are absorbed by the target tissue biomarker;
    a detector that detects pressure signals produced from the at least one target tissue biomarker in the target tissue in response to illumination of the target tissue via the illumination device; and
    one or more processors that are configured to reconstruct a quantitative tomographic image of a spatial distribution of a concentration of the at least one target tissue biomarker in the target tissue by:
      applying an inversion scheme to the pressure signals to provide a reconstructed optoacoustic image $\psi^k(\lambda)$ at each of the different illumination wavelengths;
      separating contributions of a light fluence $U^k(\lambda)$ and an absorption coefficient $\mu^k(\lambda)$ to the reconstructed image $\psi^k(\lambda)$ at each of the illumination wavelengths using a blind source separation method, whereby the absorption coefficient $\mu^k(\lambda)$ is obtained at each of the illumination wavelengths; and
      applying a spectral processing scheme to resolve the at least one target tissue biomarker, wherein the spectral processing scheme processes, on a pixel-by-pixel basis, the absorption coefficient $\mu^k(\lambda)$ obtained at each of the illumination wavelengths to resolve the spatial distribution of the concentration of the at least one target tissue biomarker.

16. The imaging device according to claim 15, wherein the illumination device and the detector are integrated in a common measuring head.

17. The imaging device according to claim 16, wherein the measuring head comprises an array of illumination elements and sensor elements.

18. The imaging device according to claim 17, wherein the array includes at least one of:
- line-shaped arrangements of the illumination elements and the sensor elements; or
- matrix-shaped arrangements with an alternating distribution of the illumination elements and the sensor elements.

19. The imaging device according to claim 15, wherein the illumination device illuminates the target tissue along at least two different diffusive projection directions.

20. The imaging device according claim 15, wherein the illumination device and the detector are configured for at least one of:
- being arranged in a blood vessel, the illumination device including an optical fiber or a light waveguide; or
- providing contact with an outer surface of the target tissue.

21. The imaging device according to claim 15, wherein at least one of the illumination device or the detector is included in an endoscopic, laparoscopic or interstitial device.

22. The imaging device according to claim 15, wherein the one or more processors apply inverse methods and spectral processing to build an image of a blood vessel comprising a coronary or a carotid artery, wherein the image represents a spatial distribution of the bio-marker in the target tissue.

23. The method of claim 1, wherein said using the at least one spectral processing scheme comprises utilizes spectral matching of the optoacoustic images acquired at the several different illumination wavelengths.

24. The imaging device of claim 15, wherein the spectral processing scheme utilizes spectral matching of the optoacoustic images acquired at the several different illumination wavelengths.

25. A method of multi-spectral opto-acoustic tomography (MSOT) imaging of a target tissue including at least one target tissue biomarker, the method comprising:
- illuminating the target tissue using several different illumination wavelengths;
- detecting pressure signals from the at least one target tissue biomarker with a detector, wherein the pressure signals are produced in the target tissue in response to said illuminating the target tissue; and
- reconstructing a quantitative tomographic image of a spatial distribution of a concentration of the at least one target tissue biomarker in the target tissue, said reconstructing of the quantitative tomographic image comprising:
  - applying an inversion scheme to the pressure signals to provide a reconstructed optoacoustic image $\psi^k(\lambda)$ at each of the different illumination wavelengths;
  - separating contributions of a light fluence $U^k(\lambda)$ and an absorption coefficient $\mu^k(\lambda)$ to the reconstructed image $\psi^k(\lambda)$ at each of the illumination wavelengths using a blind source separation method, whereby the absorption coefficient $\mu^k(\lambda)$ is obtained at each of the illumination wavelengths; and
  - using at least one spectral processing scheme to resolve the at least one target tissue biomarker, wherein the spatial distribution of the concentration of the at least one target tissue biomarker and concentrations of background chromophores are reconstructed for every pixel k from linear equations $\mu^k(\lambda)=\alpha_{MM}(\lambda)c_{MM}^k+\alpha_1(\lambda)c_1^k+\alpha_2(\lambda)c_2^k+\ldots$ for each of the illumination wavelengths $\lambda$, wherein $\mu^k(\lambda)$ is the absorption coefficient obtained at each of the illumination wavelengths $\lambda$, wherein $\alpha_{MM}(\lambda), \alpha_1(\lambda), \alpha_2(\lambda), \ldots$ are molar extinction spectra of the target tissue biomarker and the background chromophores, respectively, wherein $c_{MM}^k$ is the concentration of the target tissue biomarker, and wherein $c_1^k, c_2^k, \ldots$ are the concentrations of the background chromophores at every pixel k.

26. The method according to claim 25, wherein the spatial distribution of the concentration $c_{MM}^k$ of the at least one target tissue biomarker and the concentrations $c_1^k, c_2^k, \ldots$ of the background chromophores are reconstructed from the linear equations for every pixel k using a linear regression method.

27. An imaging device for multi-spectral opto-acoustic tomography (MSOT) imaging of a target tissue including at least one target tissue biomarker, the imaging device comprising:
- an illumination device that comprises a light source or a light guide that transmits light from a light source, the illumination device being configured to illuminate the target tissue with at least one pulsed illumination pattern at several different illumination wavelengths that are absorbed by the target tissue biomarker;
- a detector that detects pressure signals produced from the at least one target tissue biomarker in the target tissue in response to illumination of the target tissue via the illumination device; and
- one or more processors that are configured to reconstruct a quantitative tomographic image of a spatial distribution of a concentration of the at least one target tissue biomarker in the target tissue by:
  - applying an inversion scheme to the pressure signals to provide a reconstructed optoacoustic image $\psi^k(\lambda)$ at each of the different illumination wavelengths;
  - separating contributions of a light fluence $U^k(\lambda)$ and an absorption coefficient $\mu^k(\lambda)$ to the reconstructed image $\psi^k(\lambda)$ at each of the illumination wavelengths using a blind source separation method, whereby the absorption coefficient $\mu^k(\lambda)$ is obtained at each of the illumination wavelengths; and
  - applying a spectral processing scheme to resolve the at least one target tissue biomarker, wherein the spatial distribution of the concentration of the at least one target tissue biomarker and concentrations of background chromophores are reconstructed for every pixel k from linear equations $\mu^k(\lambda)=\alpha_{MM}(\lambda)c_{MM}^k+\alpha_1(\lambda)c_1^k+\alpha_2(\lambda)c_2^k+\ldots$ for each of the illumination wavelengths $\lambda$, wherein $\mu^k(\lambda)$ is the absorption coefficient obtained at each of the illumination wavelengths $\lambda$, wherein $\alpha_{MM}(\lambda), \alpha_1(\lambda), \alpha_2(\lambda), \ldots$ are molar extinction spectra of the target tissue biomarker and the background chromophores, respectively, wherein $c_{MM}^k$ is the concentration of the target tissue biomarker, and wherein $c_1^k, c_2^k, \ldots$ are the concentrations of the background chromophores at every pixel k.

* * * * *